(12) United States Patent
Krishnan et al.

(10) Patent No.: US 10,366,202 B2
(45) Date of Patent: Jul. 30, 2019

(54) DYNAMIC MEDIA OBJECT MANAGEMENT SYSTEM

(75) Inventors: Ravindran Krishnan, Mumbai (IN);
Prakash Padmalwar, Mumbai (IN);
Paula Resetco, Westchester, PA (US)

(73) Assignee: Mach 7 Technologies, Inc., South Burlington, VT (US)

( * ) Notice: Subject to any disclaimer, the term of this patent is extended or adjusted under 35 U.S.C. 154(b) by 1161 days.

(21) Appl. No.: 12/540,242

(22) Filed: Aug. 12, 2009

(65) Prior Publication Data

US 2010/0042653 A1    Feb. 18, 2010

Related U.S. Application Data

(60) Provisional application No. 61/136,156, filed on Aug. 14, 2008.

(51) Int. Cl.
*G06F 19/00* (2018.01)

(52) U.S. Cl.
CPC .................. *G06F 19/321* (2013.01)

(58) Field of Classification Search
CPC ... A61B 5/0073; A61B 5/0091; A61B 5/0476; G06T 7/0012; G06T 2207/10016; G06T 2207/10116; G06F 19/3487; G06F 21/32
USPC ............................................................ 705/3
See application file for complete search history.

(56) References Cited

U.S. PATENT DOCUMENTS

| 6,289,115 B1 * | 9/2001 | Takeo | G06F 19/321 |
| | | | 128/920 |
| 6,574,629 B1 * | 6/2003 | Cooke, Jr. | G06F 16/40 |
| 2004/0143458 A1 * | 7/2004 | Pulkkinen | G06Q 10/00 |
| | | | 705/2 |
| 2004/0249677 A1 | 12/2004 | Datta et al. | |
| 2006/0073127 A1 * | 4/2006 | Kowalik | C12N 15/111 |
| | | | 424/93.21 |
| 2006/0101154 A1 | 5/2006 | Becker et al. | |
| 2006/0242148 A1 | 10/2006 | Rothpearl et al. | |
| 2008/0021740 A1 * | 1/2008 | Beane | G06F 19/321 |
| | | | 705/3 |
| 2008/0059238 A1 | 3/2008 | Park et al. | |
| 2008/0137922 A1 | 6/2008 | Catallo et al. | |

\* cited by examiner

*Primary Examiner* — Reginald R Reyes
(74) *Attorney, Agent, or Firm* — James Marc Leas

(57) ABSTRACT

A dynamic media object management system that communicates media objects such as imagery with source media modalities including medical imaging systems and media archival, review, and analysis workstations, among other types of systems. The system includes a management console with a user interactive subsystems controller that may include one or more parameter databases populated via the user interactive subsystems controller with media tag transfer syntaxes, media format mapping protocols, compatibility matrices, and media processing rules that may include technologist reviewer routing rules, \communication schedules, and other types of predetermined and, or predefined parameters. The system may also include, among other components, a modality services subsystem that can communicate media objects within and outside the system. A media object processor interoperates with the system components and dynamically normalizes and maps and routes and schedules the media objects to the specifications of the user, for high-speed communication with the workstations.

45 Claims, 7 Drawing Sheets

DYNAMIC MEDIA OBJECT MANAGEMENT SYSTEM

PRIORITY CLAIM TO RELATED APPLICATION

This non-provisional continuation-in-part application claims the benefit of the earlier filing date of commonly owned U.S. Provisional Patent Application No. 61/136,156 filed Aug. 14, 2008, and entitled System and Method for Managing Image Files in the names of Shital Padmalwar and co-inventor Prakash Padmalwar, which is hereby incorporated by reference in its entirety as though fully set forth herein.

BACKGROUND OF THE INVENTION

Field of the Invention

This invention relates to the field of information technology and more specifically to the field of high throughput optimized information and media object management normalization, mapping, and routing across incompatible information technology infrastructures and modalities for media object generation.

Description of Related Art

What has long been needed in the field of information technology art generally and the specialized field of real-time media object management is a throughput optimized, high-speed, dynamic and on-demand media object management system that addresses the many issues surrounding prior art systems and their inherent incompatibilities. More importantly, an improved dynamic media object management system is needed that enables compatibility between many proprietary vendor source modalities. It is also desirable to create a means to enable compatibility between the many types of media object reviewing and processing technologist workstations.

More preferably, a dynamic media object management system could be created that enables previously incompatible source media modalities and technologist workstations to compatibly communicate information in a way that establishes throughput optimized and high-speed communications of media objects between myriad types of text, image, audio, video, and audiovisual source media modalities. This capability is needed in many industries, which presently must hire expensive consultancies to design custom hardware and software solutions to accomplish it. Such purported solutions require further substantial investments in specialized and highly skilled technical services professionals who are capable of merging and adapting data from legacy systems into such newly designed hardware and software systems. In other prior examples, legacy systems also included at extra cost, quality control (QC) workstations to which all media was routed for manual user review and correction.

In the present age of increasing implementation of current-day information technology solutions, many legacy text, audio, image, and audiovisual or video systems already form the currently available infrastructure. Such legacy systems continue to produce, generate, create, capture, and communicate a wide variety of electronically embodied information or media objects that are available in and communicated through a variety of vendor-specific, vendor-proprietary, and/or industry-standard information formats. The large number of different types of such legacy systems and correspondingly large number of formats has resulted in many challenges due to the incompatibilities between such systems and formats. One particularly challenging area of incompatibilities is illustrated with respect to the medical imaging field of technology.

For example, computed tomography (CT) imaging, magnetic resonance imaging (MRI), and other digital and digitally manifested diagnostic imaging systems or modalities were introduced during the 1970s. Those legacy systems have since been and are presently confronted with the increased use of specialized and general purpose computing systems that are being used to capture, store, analyze, modify, and communicate such imagery and related information for a variety of medical research and clinical applications. The need to communicate diagnostic imaging studies or media objects between different legacy medical imaging systems and modalities, other associated software applications, more modern-day clinical software systems such as Electronic Medical Records (EMRs), and alternative research computing systems has been extraordinarily difficult.

In an effort to address these many difficulties in the medical imaging field of technology, the American College of Radiology (ACR) and the National Electrical Manufacturers Association (NEMA) developed a vendor-independent standard for digital medical images that specified the file format and network protocol as well as the syntax of the associated information exchanged between systems. This Standard, designated the Digital Imaging and Communications in Medicine (DICOM), arose in an attempt to promote compatibility and standardize the exchange of digital information between diagnostic medical imaging equipment and systems vendors. More information is available at the internet website identified as "medical.nema.org". This attempt to promote compatibility between such imaging systems also sought to promote the compatible exchange of information for clinical analysis, review, archival, and communications systems, which includes Picture Archive and Communication Systems (PACS) and other computing system workstations. See, e.g., "www.imagingeconomics.com/issues/articles/2005-05_01.asp" and "en .wikipedia.org/wiki/Picture_archiving_and_communication_system".

The DICOM Standard was generated to promote the compatible capture, storage, and communication of pixel data or data streams or media objects that represent each image within an imaging study as created or generated by an imaging device or modality. In addition to compatible capture, storage, and communication of such media objects, the DICOM Standard was also intended to address the compatible inclusion, appending, or combination of specific ancillary media object information regarding the image and the overall study being captured, stored, or communicated. For example, such ancillary data is preferably stored within what are referred to as DICOM Attribute Tags, which are combined, stored, and communicated with each media object or image or imaging study.

As a further example, the types of information that may be contained within DICOM Attribute Tags may also preferably include statistics about the medical imaging device or modality that generated the image and/or study. Such information may also include the modality's unique ID, the date and time when the images or study were taken, and/or name of the technologist or operator who performed the study. For certain types of medical imaging applications, such information may also include information on the procedure such as procedure code, biological tissue type and/or body part, institution where the procedure was performed, name of the physician who ordered the study or research, and the radiologist who is scheduled to read the study. Patient specific information may also be encoded within an image or study and contained within DICOM Attribute Tags such as patient name and identifying numbers, date of birth, sex, and other related data.

Despite the efforts to increase compatibility between such legacy systems, many vendors have availed themselves of the flexibility that was built into the DICOM standard. In the past, many organizations implemented vendor specific and exclusive installations. However, as the number of vendors and manufacturers of such systems has increased, such organizations have sought to create best-of-class capabilities by incorporating those elements of each vendor-specific system that offered the best performance and the most attractive cost. These efforts to establish customized, best-of-class installations, has resulted in the need to overcome incompatibilities between vendor-specific systems that implement a vendor-specific version of the respective DICOM standard through customization. This, in turn requires expensive investments in workstations for skilled QC technologists and/or skilled consultancies having the technical expertise to create such customized solutions that suit the requirements of the particular installation or user.

As a further example of the types of challenging incompatibilities that need to be overcome, imaging studies may be generated by a vendor-specific system that may incorporate a DICOM compatible, but vendor unique media object(s) containing image information and pixel data or image or image series representations.

In many more modern technologist and clinician data processors or workstations, or PACS workstations, the reviewer may create text-based and graphically-represented annotations that are also stored in the media object as ancillary information appended to the image information. Additionally, many such systems generate ancillary information that describes prior created media objects or imaging studies so that a technologist or reviewer may consider a temporal dimension in their analysis of such media objects. When communicated to the system or modality of another vendor viewing or analysis data processing workstation, the communicated media object may be displayed with such image information in an improper anatomical order, without the information related to prior created media objects and imaging studies, and with garbled or incomprehensible image and related ancillary annotations and information.

One reason for these challenges and problems stems from the flexibility that was built into the DICOM standard, and which allows for the use of vendor-specific, private, and/or proprietary DICOM Attribute Tags or ancillary information. The DICOM availability of such vendor specific tags was intended to define ancillary information that could be used for vendor specific purposes to facilitate internal communications within the vendor's product set. While this flexibility might have been of use to vendors, such flexibility has created obstacles to the goal of sharing compatible media objects such as diagnostic studies between different systems for the purpose of sharing medical records, including clinical Electronic Medical Record (EMR) systems.

Many vendors have sometimes even created incompatibilities between different systems within their own product lines. Combined with the differences between products, systems, and modalities from different vendors, the DICOM standardization attempts have fallen short of the originally intended goals. This shortcoming amplifies the need for a means to enable compatible communication of media objects between such systems and installations.

In a more detailed example of the problems that stem from incompatibilities between vendor-specific versions of the DICOM standard, a particular vendor specific imaging system or modality may generate, capture, and/or create a media object that includes imaging as well as ancillary information such as: a study description, a modality code, and an organ code, among other information. Upon generation, the media object (images and ancillary information) is communicated to another viewing, analysis, and/or archival and storage system, such as a PACS data processor or workstation. After communication to the same-vendor PACS workstation for review and analysis by a clinician technologist, or radiologist, the same-vendor PACS workstation will ideally also automatically display historical and/or prior related media objects. Such PACS systems thereby enable the technologist, clinician, or radiologist to review historical information and images to consider changes in the images over a span of time.

The automated display of such prior generated media objects is only possible if the ancillary information of the prior-generated and newly communicated media objects is an identical match. Those experienced in the field of art may appreciate that this is impossible even in same-vendor installations having multiple same-vendor versions of similar imaging systems and modalities due implementation flexibilities afforded by these types of systems.

Such incompatibility is even more pronounced between imaging systems and modalities from different vendors. The challenges are even greater for users and installations that attempt to establish best of class facilities using the systems, modalities, devices, components, and equipment from many vendors. Another dimension of complexity is introduced where installations such as imaging centers and medical institutions attempt to collaborate or are required to share information subsequent to a corporate merger. Even within collaborating and/or co-owned facilities, use of slightly different nomenclature in the ancillary information can create incompatible attribute values or DICOM attribute tag values such that the downstream workstations or PACS workstation may not recognize related historical information.

In the continuing example of possible incompatibilities resulting from flexibility of the DICOM standards, many other DICOM specific issues create opportunities for improvement. One such opportunity includes the specific format compatibility for pixel and ancillary information data streams, which identify how an imaging study can be stored, transmitted, and communicated in a particular sequence.

Another such opportunity includes creating compatibility for ancillary information terms with regard to image series levels, which describe specific subsets of imaging series contained within a given image study to allow for reduced networking loads when accomplishing series level routing. Another opportunity and DICOM specific area for improvement where many incompatibility problems have been encountered includes the DICOM defined query/retrieve model levels, which those having skill in the area refer to as a patient or study root.

DICOM attribute tags also need a more compatible communications capability because vendor specific systems have the ability to generate updated ancillary information that is only visible on same-vendor systems but appear as empty and/or incorrect ancillary information in the created media objects o non same-vendor specific systems. This in turn creates errors in downstream, non same-vendor system or workstations that are receiving these media objects.

The DICOM standard has also seen short-comings in vendor-proprietary and specific implementations of what is referred to as compression and transfer syntax, which is supposed to be used by the imaging system or modality to enable communication to reviewing, analysis, and archival data processors and workstations such as PACS workstations. More often than not, however, such compatibility is advertised but unrealized, which usually requires expensive and time-consuming intervention by highly skilled service providers having the expertise to create a customized hardware and/or software solution to enable the required communication compatibility between same-vendor as well as installations populated with systems, modalities, and equipment from various vendors. Such customized solutions are also largely inflexible, as the introduction of updated same-vendor equipment and software or different vendor options requires yet more new and custom solutions.

Despite many attempts, modality, workstation, and information technology infrastructure manufacturers, service providers, users, and operators have been frustrated by the unavailability of high throughput and compatibility improving technologies and systems, despite the need for and possibility of improvements. The information technology market continues to seek a higher-throughput optimized, high-speed, real-time or dynamic media object management system.

Even more preferably, such an improved system should incorporate all of the advantages of the prior art while enabling compatibility across proprietary and previously incompatible vendor source modalities and workstations, while offering reduced costs of operation, greater ease of use, and more effective and time-saving media object management options. As used herein, the term modality is defined to mean any type of hardware and software device, component, equipment, machine, system, and combinations thereof that are capable of and/or used to create, generate, capture, modify, and communicate source media objects as discussed elsewhere herein.

SUMMARY OF THE INVENTION

Many of the problems of the prior art and sought after improvements in the highly specialized field of high throughput, information technology, especially text, audio, image, and audiovisual media object management, are solved with the innovative dynamic media object management system of the invention. The improvements described herein enable previously unavailable capabilities, most notably, high speed and automated processing and communications between generally incompatible and proprietary, vendor specific equipment and systems.

In one preferred configuration of the invention, a dynamic media object management system may be implemented on a specialized and/or general purpose computer, data processor, or workstation. Any of such variants will preferably incorporate one or more or at least one hardware or virtualized central processing unit(s) (CPU) in communication with temporary and permanent storage media, and a wireless and/or wired network communications interface, among other types of well known peripherals.

Temporary and permanent storage media are often referred to by those with knowledge in the field as random access memory, hard disks, rewritable optical media, thumb drives, universal serial bus or USB drives, solid state disk drives, and similar types of removable and transportable storage devices. Such peripherals may include locally and remotely connected printers, optical storage media, backup and archival data storage systems and/or file and information and data servers, and data input and output devices such as display monitors, keyboards, optical imaging scanners, and pointing and selecting devices like a mouse, tablets, and keyboards.

In specialized computer implementations of the contemplated dynamic media object management system, the various inventive components and elements may be integrated into one or more or at least one specialized and/or dedicated components and computing processors like firmware-coded processors that, unlike general purpose computers and data processors, are optimized to operate more reliably for high-demand business mission critical applications.

Such mission critical specialized components can operate possibly without the need for general purpose operating system software, which can be prone to operational disruptions from a virus, trojan horse, spyware, and other sorts of malware software that is more common to such general purpose computers and any required general purpose operating system software.

In other optionally preferred embodiments of the inventive dynamic media object management system, wherein a virtualized specialized or general purposed computing workstation configuration is contemplated, an optimally arranged hardware and software variation of the novel system is implemented that can operate upon a dedicated or shared, local or remote workstation. Such distributed computing resources and virtualized computing environments enable more efficient distributed and/or centralized data processing capabilities whereby mission critical computing resources can be made available continuously and without interruption despite the failure and/or unavailability of specific and/or individual computing processors, equipment, components, and peripherals.

For example, those having knowledge in the information technology field sometimes refer to such virtualized and/or distributed computing environments by vendor independent nomenclature that includes terms and phrase such as blade servers, server clusters, server farms, which can refer to dedicated and shared groups of CPUs, file/data servers, peripherals, and related equipment and components. Such virtualized computing environments may also include integrated and/or complementary virtualization software capabilities that can further enable use of the inventive dynamic media object management system. Such virtualization computing capabilities for use in such virtualized computing environments can include, for purposes of example but not limitation, software available from Sun Microsystems, which is known to those skilled in the related arts as VMWare and/or Virtual Box.

The contemplated dynamic media object management system may also be configured wherein its various components and elements are embodied or coded in the storage media of the general purpose or specialized computer to transform the CPU thereof into the specialized, new dynamic media object management system. The dynamic media object management system described here therefore means the dynamic media object management system as it is embodied and operable as a specialized data processor or specialized computer or thereby specialized, general purpose computer and general purpose operating system. In these configurations, the dynamic media object management system, in conjunction and/or cooperation with the noted additional hardware elements, functions therewith to establish the specialized, high-throughput, high-speed, and real time dynamic media object management system.

The dynamic media object management system preferably incorporates one or more of at least one network interface(s) and is thereby in communication with at least one, or one or more, source media modality(ies) (SMMs) that generate and/or communicate source media objects (SMOs) or source media or media objects to and/or from the dynamic media object management system. SMM is defined here to include any number of systems, equipment, devices, and components that can create, generate, modify, and communicate SMOs. While some examples described herein refer to medical industry imaging systems and modalities, the invention is directed to a much larger universe of SMMs.

For example, SMMs can include scanning equipment capable of scanning paper-based text and images into text-based and image-based data files and/or optically character recognized (OCR) data that can represent such originally paper-based items. Each such data file can represent one or more or at least one such pages of information, and each such data file is typically referred to here as the SMO or source media, which can be communicated to and from and between the SMM scanning equipment and the dynamic media object management system. For such image-based SMOs, the phrase image media objects (IMOs) and image object processor (IOP) may also be used.

Additionally, other examples of SMMs include audio recording devices that can convert audible information such as voice, music, and other audible sounds into analog and/or digital recordings, which can be communicated to and from such recording devices to the dynamic media object management system. In this example, such audio recordings are also defined to be SMOs or source media.

In still other examples, SMMs can be audiovisual and/or video recording devices such as video cameras that convert visually and/or audibly perceptible light and sound information into analog and digital recordings, which can be communicated as source media or SMOs to the dynamic media object management system of the invention.

SMMs as contemplated for purposes of the invention may also be radiological, nuclear, ultrasonic, eddy current, x-ray, magnetic resonance, computed tomography, radar, sonar, lidar (light detection and ranging), laser, microwave, and similarly capable analog and digital imaging devices. Such devices can typically emit and detect many types of electromagnetic signals and energy including without limitation radiographic, ultrasonic, radar, microwave, electron, electronic eddy current, x-ray, laser, and any other type of electromagnetic signals and energy (including for example but not limitation, radio, microwave, x-ray, and laser frequency energy).

Such SMM devices can also typically detect and/or cooperate with other devices that can detect the resulting reflected and pass-through energy and signals, and which can convert such into images and representations of physical structures, biological tissues, marine and aviation environments. These SMMs can be manifested in various types of equipment including without limitation non-destructive testing, inspection, and evaluation devices (NDEs/NDIs), marine sonar systems, aviation and military radar systems, stereotactic imaging and range finding devices, and medical imaging devices, to name only a few types of such devices. As contemplated for purposes of the invention described here, all such known and relevant legacy and current-day SMMs are capable of creating, modifying, and/or communicating to and from the dynamic media object management system, the resulting source analog and digitally embodied images and representations of source media as the SMOs.

The dynamic media object management system also preferably communicates with one or more or at least one technologist workstations or data processors (TDP) to communicate SMOs there between for additional review, analysis, post-processing, and storage. For certain applications, the TDPs may also be denoted as image review workstations (IRWs). The TDPs may be other SMMs, other dynamic media object management systems, and/or other specialized or general purpose computer workstations having one or more of the noted peripherals.

In the example of sonar or radar systems, such TDPs can be local integral and/or remote radar and sonar operator workstations, and combinations thereof. In the example of NDEs/NDIs, the TDPs can be local integral and/or remote viewing and analysis workstations, and combinations thereof. For the examples of medical imaging devices that may include x-ray, ultrasound, computed tomography, magnetic resonance devices, and the like, the TDPs can be one or more locally integrated and/or remote clinical or diagnostic viewing workstations. Such TDPs may also preferably and optionally include, one or more or at least one local integral and/or remote viewing archival, reviewing, and/or analysis workstations such as PACS or Quality Control (QC) workstations, and remote clinician or technologist viewing data processors and workstations. Such TDPs may also preferably and optionally include, one or more or at least one local integral and/or remote post processing workstation whereby SMOs are manually or automatically updated, adjusted, or enhanced.

In one optionally preferred variation of the dynamic media object management system, one or more or at least one management console (MC) is incorporated, which preferably includes a user interactive subsystems controller (UISC). The MC is preferably implemented in cooperation with, as an integral part of, and/or as a local or remote distributed component of the dynamic media object management system. More preferably, the MC is configured with the UISC to be the primary user or operator interface with the dynamic media object management system.

In additionally preferred and optional variations, the MC and UISC also incorporate a graphical user interface (GUI) that can communicate with peripherals such as the display screens and input and output devices described elsewhere herein. The MC and UISC also optionally includes one or more or at least one parameter database in communication with the MC and UISC and operative to receive, store, and communicate predefined, user defined, and preferred system parameters useful for operation and configuration of the dynamic media object management system. Even though the parameter database is described here for purposes of illustration as being a part of the MC and/or UISC, the parameter database may additionally be incorporated as a local and integral or remote and independent element of the dynamic media object management system itself.

Although often used herein in the singular form, the word parameter is defined to include a single parameter, a group of parameters, single and multidimensional parameter vectors and matrices, arrays of parameters, data streams and groups and arrays of data streams, multivariable functions, and the like, as those terms and phrases may be used by those skilled in the science, engineering, mathematical, and information technology fields of art.

In other preferably optional modifications to the embodiments of the inventive dynamic media object management system, one or more or at least one modality services subsystem(s) (MSS) is incorporated that communicates with the MC. The MSS also preferably may include a source media object (SMO) queue configured to receive, store, and communicate SMOs. More preferably, the MSS may also incorporate one or more or at least one source modality operations list (MOL). For imaging specific variations of the invention, the MSS may also be referred to as an image services subsystem (ISS) and the SMO queue may be referred to as an image management queue (IMO queue).

The MOL can be part of or independent from the parameter database. The MOL defines and enables the applicable, preferred, and/or required mode of operation of the SMM to enable an operator or technologist to operate the SMM easily, consistently, and properly, and with a minimized likelihood of error. More preferably, the technician, operator, and/or user of the SMM may query the MOL via the dynamic media object management system during operation of the SMM to enable rapid and consistent operation of the SMM. This capability can enable more consistent use of geographically disparate SMMs as well as comparably consistent use and application of dissimilar but similarly capable SMMs.

Additionally, the MOL may also include and/or append to the SMOs appropriate, preferred, or required information that may preferably be included and/or form a part of the SMOs. Such information may include modality specific information, date, time, operator identification, as well as information specific to the SMOs.

For example, in NDI/NDE applications, the MOL can enable the consistent inclusion or appending of information regarding the physical structure being examined to respective SMOs. In the paper-based scanning and imaging example, the MOL may append information related to the paper-based media being scanned, OCRed, and imaged. In the aviation environment example, radar operators may use the MOL to tag the SMOs with target aircraft identifying information in addition to the other described information. In the marine environment example, sonar operators may identify information related to specific fishing area information to be added to the SMOs. Military sonar and radar operators may employ the MOL to more easily and accurately append target and/or threat specific information to SMOs.

In the audio SMM embodiment of the invention, information regarding the audio recordings may be appended to the SMOs. Such audio related information can include, for purposes of example without limitation, information related to: the recorded music and artist, recorded medical clinician notes, recorded deposition testimony, recorded voice messages, and/or any other information relevant to the recorded audio information, which may be suited for inclusion with and/or appending to the SMOs.

In the medical imaging example of the dynamic media object management system, the MOL is often referred to by those skilled in the medical imaging field as a modality work list (MWL). In that specific example of the dynamic media object management system, SMM technologists, technicians, and operators can more easily and more accurately append the SMOs with respective information regarding the biological tissues being imaged and studied, which may also preferably include information regarding patients whose biological tissues are being examined. In the medical imaging and non-medical imaging contemplated embodiments, the inventive system may also be referred to as a dynamic image management system.

In other optionally preferred variations of these embodiments, the dynamic media object management system may also include one or more or at least one media object processor (MOP) in communication with the MC and other components of the dynamic media object management system. More preferably, the MOP interoperates with the dynamic media object management system and receives and processes SMOs. Even more preferably, the MOP is configured to enable compatibility between SMMs and TDPs in ways that establishes greatly increased through-put and communication of SMOs there between. This is accomplished by the MOP, which may use one or more predefined parameters from the parameter database to normalize all or part of the information and format of the SMOs for faster and compatible communication and routing to other SMMs, TDPs, and any other target device that is to receive SMOs.

The dynamic media object management system may also be optionally modified to incorporate predefined parameters that establish one or more or at least one predetermined, preferred, and/or predefined SMO communications schedule parameter(s). Such predefined schedule parameters may be employed to optimize communication of SMOs during times when communications networks have more available bandwidth, which improves throughput and speeds up communications. In addition, such predefined schedule parameters may establish one or more predetermined times when SMOs are to be communicated.

The dynamic media object management system may also preferably include one or more optionally desired predefined routing parameter(s) that can be included in the parameter database via the user interface of the UISC to establish preferred, required, and/or desired routing rules. Such routing rules may enable the MOP or other components of the dynamic media object management system to direct, route, and/or communicate SMOs to one or more or at least one TDPs.

Other possibly preferable embodiments of the MC, MSS, and/or parameter database may optionally include one or more or at least one predetermined transfer syntax parameter, which establishes a transfer syntax operative with the MOP to normalize the SMOs to enable compatible communication of the SMOs to the at least one TDP. More preferably, and for purposes of further example, the transfer syntax will optionally incorporate SMM and TDP compatibility data that enables the MOP to update only that information in the SMOs that may need to be normalized or modified for compatible communications between the SMMs, TDPs, and other elements of the dynamic media object management system. By only updating those elements of SMOs required for compatible communications, increased throughput may be possible, as well as higher speed communication of SMOs.

Other optional modifications to any of the embodiments of the invention may also preferably include one or more or at least one predetermined or predefined mapping parameter that establishes a mapping protocol. Such a possibly preferred mapping protocol parameter or parameters may be stored in any one or more of the contemplated parameter databases.

For purposes of further exemplary but non-limited illustration, the predetermined mapping parameter and associated mapping protocol may enable the MOP or other components of the dynamic media object management system to rapidly, in real-time, dynamically, and compatibly communicate SMOs. Such communications may thereby be preferably achieved between nominally incompatible SMMs, TDPs, and related devices, components, equipment, as well as with any part of the inventive dynamic media object management system.

The dynamic media object management system may also be optionally adapted to preferably incorporate one or more or at least one multimode updater (MU) that may be responsive to one or more or at least one predetermined update parameter. The MU may be preferably or optionally configured to operate in one or more or at least one mode(s). One possibly preferred and optional mode may include for purposes of example without limitation, a scheduled SMO group or batch update mode wherein an entire store or group of SMOs are updated periodically or one-time according to a possibly preferred scheduled time and/or date.

Another possibly preferred MU mode includes an on-demand and/or upon-command single update or selected SMO update operational mode, wherein a specifically identified or group of specifically identified SMOs are updated. In yet another optionally preferred mode of MU operation, a real-time or dynamic, on-the-fly continuous SMO update mode wherein SMOs are updated during processing or as SMOs are communicated during other processing operations.

More preferably, the MU is operative to update SMOs that may be stored anywhere including whether stored on SMMs, TDPs, and anywhere else in the dynamic media object management system, using one or more of the contemplated updated parameters. Also the update parameter may preferably establish an optionally desirable compare and update rule or set of rules that can be employed by the MU to update information that may be appended to and/or included with the SMOs so as to enable increased throughput compatibility as between SMM, TDPs, and any elements of the inventive system.

These variations, modifications, and alterations of the various preferred and optional embodiments of the inventive dynamic media object management system may be used either alone or in combination with one another and with the features and elements already known in the prior art and also herein described. Such embodiments can be better understood by those with relevant skills in the art with reference to the following detailed description of the preferred embodiments and the accompanying figures and drawings.

BRIEF DESCRIPTION OF THE DRAWING(S)

Without limiting the scope of the present invention as claimed below and referring now to the drawings and figures, wherein like reference numerals, and like numerals with primes, across the drawings, figures, and views refer to identical, corresponding, or equivalent elements, methods, components, features, and systems:

Figure 7:
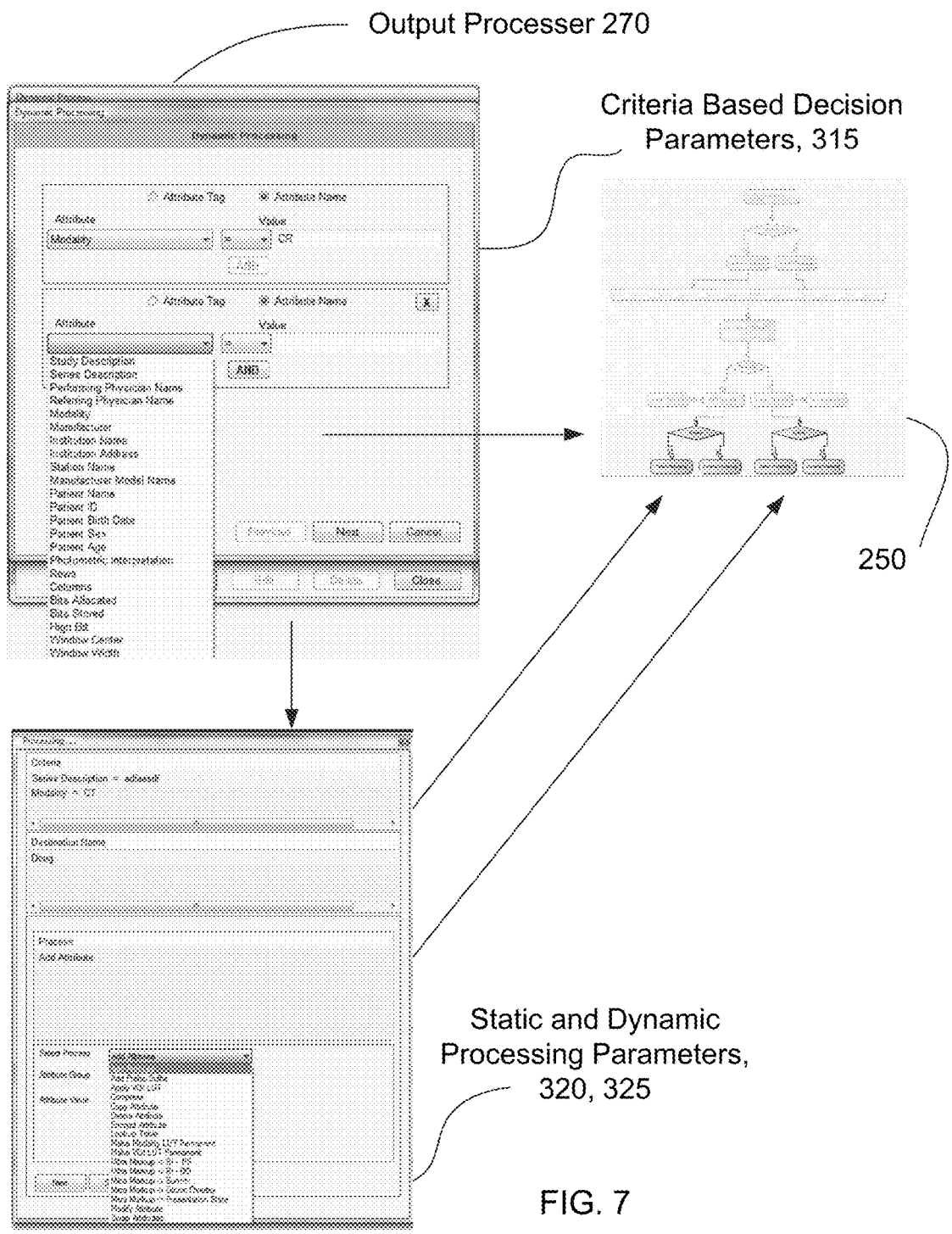

FIG. 7 describes an additional component of the dynamic media object management system of the preceding figures.

DETAILED DESCRIPTION OF THE INVENTION

Figure 1:
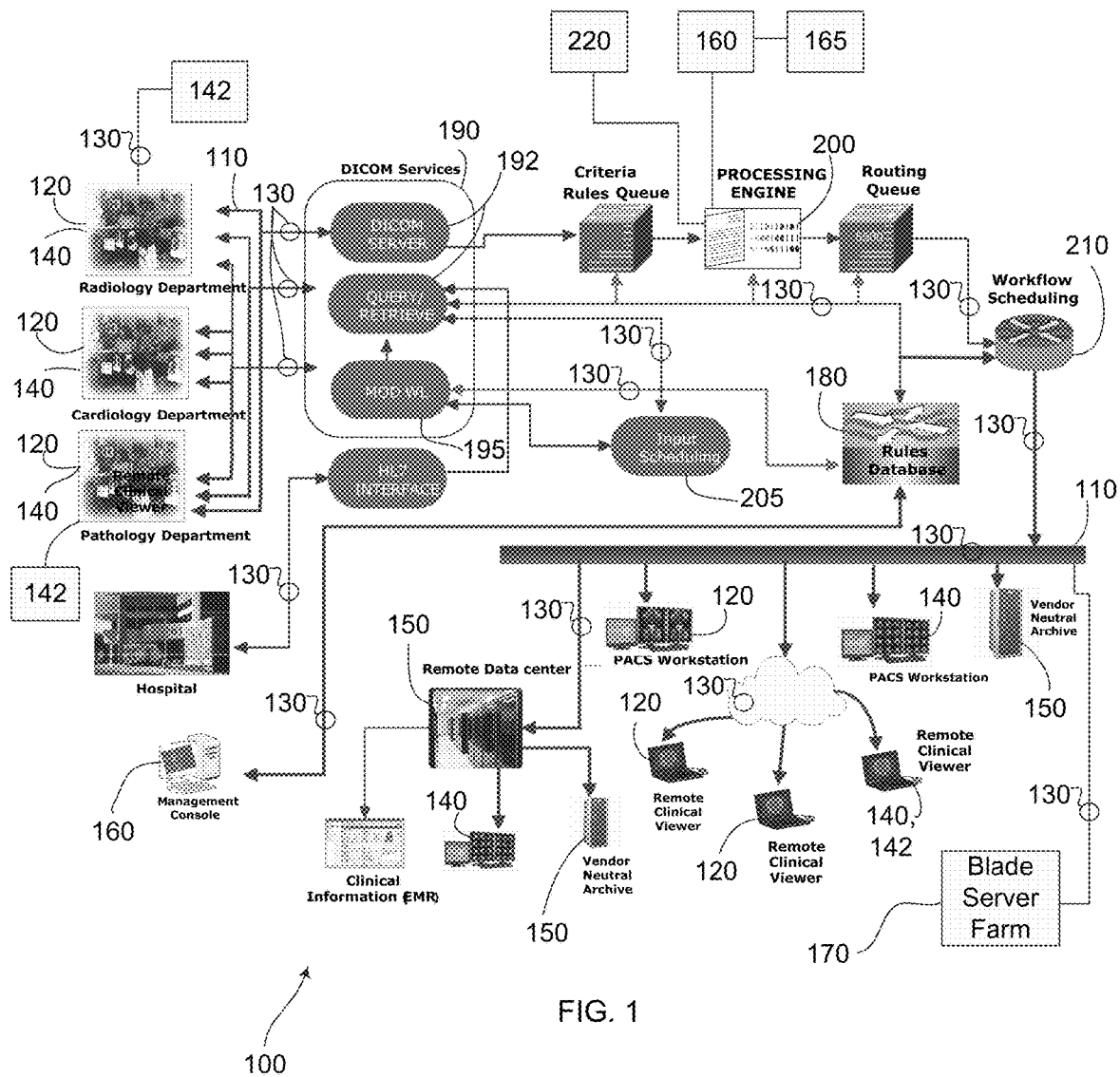
FIG. 1 is a schematic of the inventive dynamic media object management system implemented to establish compatible communications with previously incompatible hardware and software systems, equipment, devices, and components.
Figure 2:
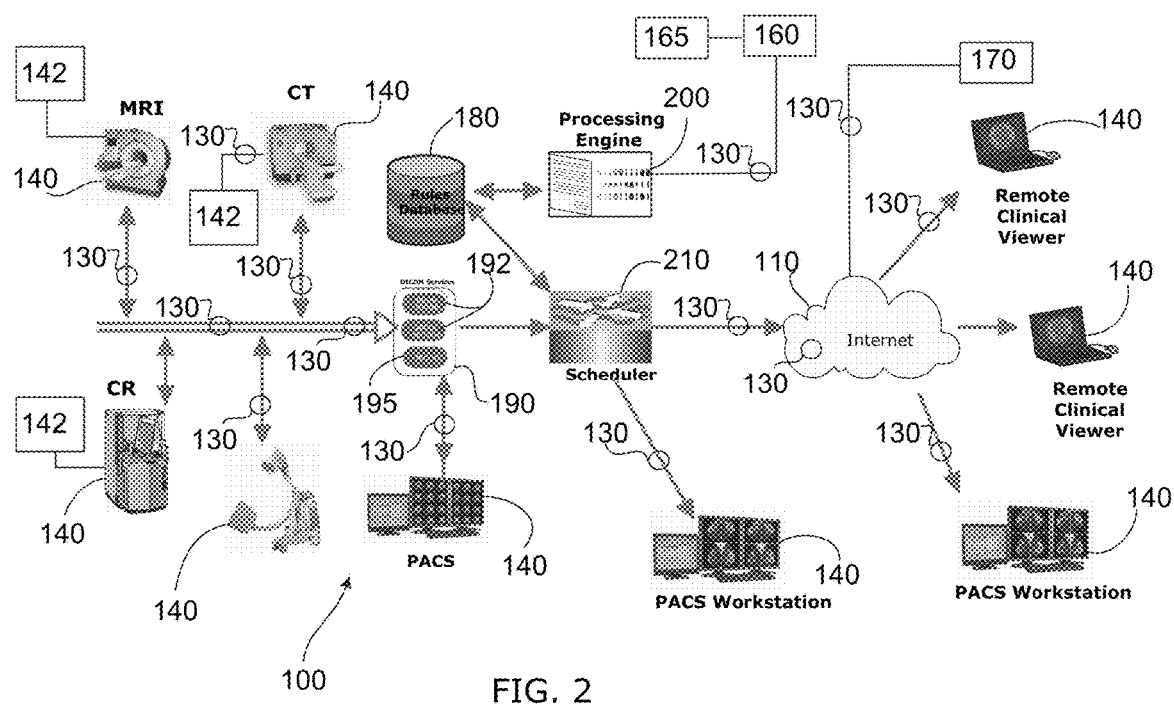
FIG. 2 is another schematic of an optionally preferred embodiment of the novel dynamic data object management system of FIG. 1 also establishing compatible communications with dissimilar hardware and software systems and equipment.
Figure 3:
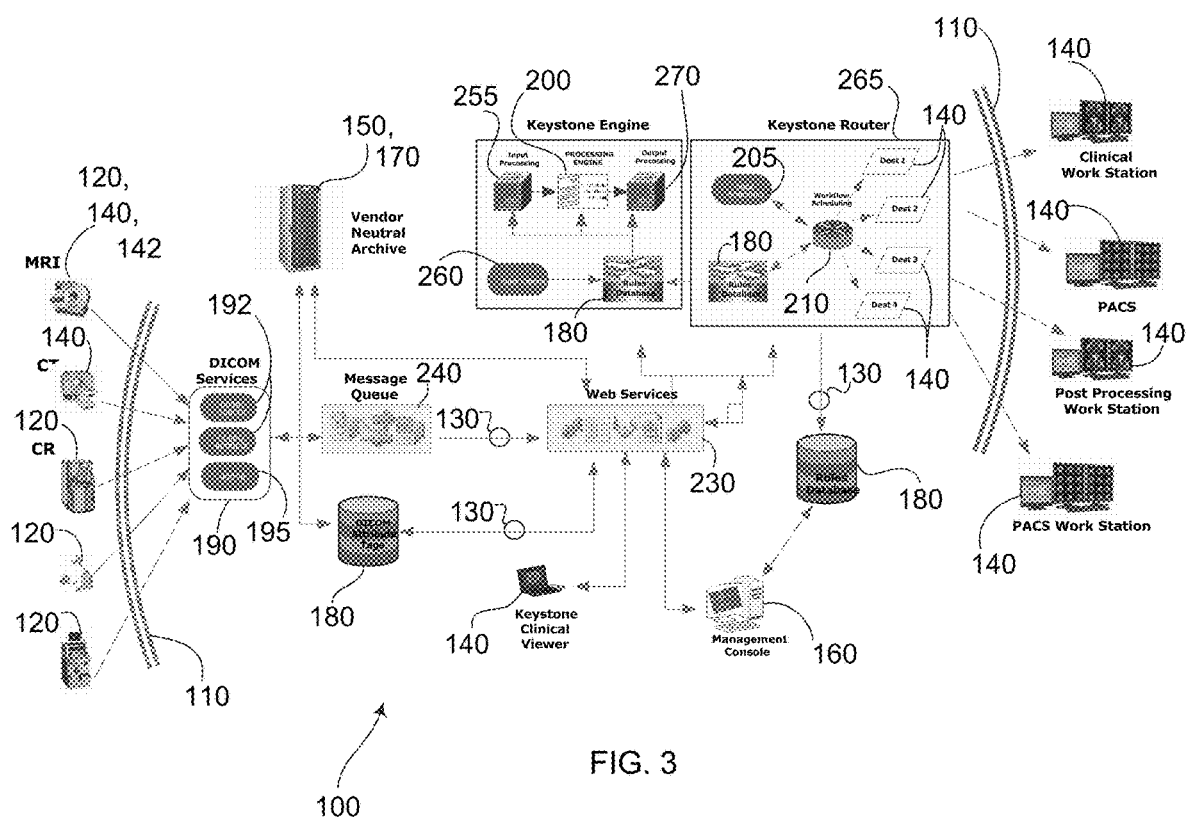
FIG. 3 is another schematic representation of the dynamic media object management system of FIGS. 1 and 2.

With reference to FIGS. 1 through 7, and specifically to FIGS. 1, 2, and 3, various preferred and optionally preferred embodiments of the dynamic media object management system are now described in more detail.

In one such preferred configuration of the invention, the dynamic media object management system 100 is embodied as a one more or at least one specific and/or virtualized, specialized and/or general purpose computer, data processor, and/or computing workstation, in any of the variations already described. More specifically, the dynamic media object management system 100 includes one or more or at least one network interface 110 that establishes communication with at least one, or one or more, source media modality(ies) (SMMs) 120. The SMMs 120 create, capture, generate, and communicate source media objects (SMOs) or source media or media objects 130 to the dynamic media object management system 100. As noted elsewhere herein, the SMMs 120 include scanning and imaging equipment 120 that enables scanning paper-based text and images, audio recording devices, and audiovisual and/or video recording devices 120.

The dynamic media object management system 100 preferably communicates with one or more or at least one technologist workstations or data processors (TDP) 140 and communicates SMOs 130 there between for analysis, review, storage, and additional and post-processing of the SMOs 130. The TDPs 140 may also be termed image review workstations (IRWs) 140 for various imaging applications. The TDPs 140 are depicted generally as data processors and technologist workstations, but may also be SMMs 120 adapted to receive SMOs and related information at same-vendor and/or vendor specific TDPs 142, other dynamic media object management systems (not shown but similar configured to system 100), and/or other workstations, and peripherals. Such other types of workstations and peripherals may also include remote data centers 145 and vendor neutral and/or vendor independent archival data centers 150, servers 150, server clusters and farms 150, and the like.

In modifications of any of the preferable or optional arrangements of the dynamic media object management system 100, one or more or at least one management console (MC) 160 may be included. More preferably, another variation of any of the configurations of the invention may include a user interactive subsystems controller (UISC) 165. The MC 160 may also preferably be configured as an integral part of, and/or as a local or remote and distributed computing resource 170 of the dynamic media object management system 100 using the virtualized or other type of distributed computing capabilities described elsewhere herein.

The MC 160 may also be optionally configured independent of and/or as part of or in cooperation with the UISC 165 to be an interface, for a primary user or operator, with the dynamic media object management system 100. In certain optionally preferred configurations, the MC 160 and UISC 165 may also further include a graphical user interface (GUI) operative to communicate with user displays, and input and output devices described elsewhere herein.

The MC 160 and UISC 165 may also optionally cooperate and/or communicate with, and/or include one or more or at least one parameter database and/or database engine 180. In optionally preferred configurations, such parameter databases 180 are interoperable with the many components and elements of the dynamic media object management system 100. More preferably the contemplated preferred and modified variations of the parameter databases 180 may also be operative to receive, store, and communicate predefined, predetermined, user defined, and/or preferred system parameters.

Such predefined, predetermined, and/or dynamically updated parameters may also include SMO processing parameters that enable or establish communications scheduling, SMO routing, transfer syntaxes, and mapping protocols. Such parameters may also preferably include comparison and update rules, queries, SMM operations lists (OLs) and modality work lists (MWLs), electronic medical or health records (EMRs, EHRs), and nearly any other type of parameters useful for configuration and operation of the dynamic media object management system 100.

The parameter databases 180 are described in most contexts herein for purposes of illustration as being a local and integral component or part of the MC 160 and/or UISC 165. However, the parameter database 180 preferably may also be incorporated as a local and integrated part or component of any other part of the dynamic media object management system 100. Also preferably, any or all of the parameter databases 180 may be local and/or remote and independent but cooperative elements of the dynamic media object management system 100, and operative via any of the contemplated distributed computing elements 170.

In still other equally preferable variations of any of the embodiments of the dynamic media object management system 100, one or more or at least one modality services subsystem (MSS) 190 is interoperably arranged with the system 100 and may preferably communicate primarily with the MC 160. More preferably, the MSS 190 optionally includes one or more or at least one source media object (SMO) queue 192 that is configured to receive, store, and communicate SMOs 130. The MSS 190 also may optionally incorporate one or more or at least one source modality operations list (MOL) 195. The MOL 195 may be an integral part of or independent from the parameter databases 180 and may instead be a remote and distributively operating component. In further alternatively preferred variations, the MOL 195 may also preferably form a part of any other elements of the system 100, including for purposes of example, any or all of a specific type of SMM 120 for which the MOL 195 is intended as described in more detail elsewhere herein.

In at least one embodiment of the contemplated MOL 195, the MOL 195 defines and enables the applicable, preferred, and/or required mode of operation of the SMM 120. For purposes of example but limitation, the MOL 195 thereby enables an operator or technologist to operate the SMM 120 more easily, consistently between operations, and properly according to any required methodology of operation, and with a substantially reduced likelihood of error.

In additionally preferred and optionally configurations, the technician, operator, and/or user of the SMM 120 may rapidly and instantaneously query the MOL 195 via the dynamic media object management system 100 and during operation of the SMM 120. Among many possible benefits, the MOL 195 may establish consistent methodology and use of institutionally and/or geographically disparate SMMs 120, as well as comparably consistent use and application of dissimilar models of but possibly similarly capable SMMs 120 from the same vendor.

In yet other possibly preferred alternative configurations of the MOL 195, SMOs 130 generated or created by the SMM 120 may be appended or modified to include appropriate, preferred, or required information that may be included as a part of the SMOs. Such information may include SMM-specific information, as well as date, time, operator identification, as well as information specific to the type of SMOs 130 being generated.

Such MOLs 195 are often referred to by those skilled in the medical imaging field as a modality work list (MWL) 195, which is described in part by the previously noted DICOM standard. In this specific medical industry example of the system 100, technologists, technicians, and operators of SMMs 120 may employ the MWL 195 to append the SMOs 130 with relevant information. In these contemplated medical imaging specialized applications, SMOs 130 may also be referred to as image media objects (IMOs) 130. For further illustration without limitation, such appended data may also be termed by those in the field as ancillary information forming a part of DICOM attribute tags, and may describe the biological tissues, anatomical region, and/or organ being imaged, the type of imaging study being performed, as well as EMR and EHR information unique to the patients being examined.

In the medical and non-medical imaging configurations, the system 100 may also be described as a dynamic imaging management system 100. Furthermore, in these contemplated image specialized variations, the MSS 190 may also be referred as an image services subsystem (ISS) 190 and the SMO queue 192 may be termed an image media object queue or IMO queue 192, and the MOP 200 may also be described as an image object processor (IOP) 200.

The optional and preferred embodiments of the dynamic media object management system 100 may also include one or more or at least one media object processor (MOP) 200. More preferably, the optionally included MOP 200 communicates and interoperates with the MC 160 and/or other components of the system 100. The MOP 200 also preferably receives and processes SMOs 130. In cooperation with the other many components and capabilities of the system 100, the MOP 200 also preferably enables compatibility between nominally incompatible SMMs 120 and TDPs 140.

In at least one preferred embodiment of the system 100, the MOP 200 may establish compatibility in cooperation with one or more of the parameter databases 180, by employing one or more predefined parameters. The parameters enable the MOP 200 to normalize all or part of the information and format of the SMOs 130 from any vendor-specific SMM 120 so that such information and format can be compatibly received by otherwise incompatible TDPs 140, and even other SMMs 120 and connected, same-vendor TDPs 142. Such normalized SMOs may also be thereafter communicated to any other target device needs to receive compatibly normalized SMOs 130.

Further optionally preferred variations applicable to any of the embodiments of system 100 may also include one or more or at least one input scheduler 205 in communication with the MOP 200 to poll SMMs 120 and to schedule receipt and processing of generated SMOs 130. An optionally preferred one or more or at least one workflow scheduler 210 may also be in communication with the MOP 200, which schedules routing of processed and unprocessed SMOs 130 to TDPs 140, 142, and other systems that may include archival data centers 150 and distributed computing resources 170.

The alternatively desired schedulers 205, 210 may be commanded by the MC 160, UISC 165, and/or may independently poll the parameter databases 180 for additionally preferred, predefined parameters that establish one or more or at least one predetermined, preferred, and/or predefined SMO communications schedule parameter(s). Any such schedule parameters may be employed by the schedulers 205, 210 to establish communication of SMOs 130 during predetermined times and/or during times when communications networks are less heavily burdened. In this way, the system 100, and the schedulers 205, 210 may be optimized to improve throughput and speed of the system 100.

The dynamic media object management system 100 may also optionally include one or more or at least one router 215 as part of and/or in communication with the system 100. The router 215 may be controlled by the MC 160 and/or may poll the parameter database 180 to obtain a routing parameter that establishes to which TDPs 140,142 and/or group of TDPs 140, 142 that processed or unprocessed SMOs 130 are to be communicated. Such routing capabilities may also establish where such SMOs 130 are to be communicated for storage at remote archives 150 or for further processing by distributing computing resources 170.

In other modifications to embodiments of the system 100, optionally useful predefined routing parameter(s) may be populated into one or more of the contemplated parameter databases 180 via the UISC 165 user interface, and may be configured to identify preferred, required, and/or desired routing rules. For example, such routing rules may establish how the router 215 is to direct, route, and/or communicate SMOs 130 to one or more or at least one of the TDPs 140, 142, or other components of system 100 or to other resources 150, 170.

The dynamic media object management system 100 also contemplates optionally preferred variations wherein the MC 160, parameter databases 180, MSS 190, and/or MOP 200 may include and/or employ one or more or at least one predetermined transfer syntax parameter. Such transfer syntax parameters are more preferably multi-dimensional rules that enable the system 100 to compatibly communicate SMOs 130 between otherwise incompatible SMMs 120, TDPs 140, 142, and other systems and components.

More specifically and as a further example, any vendor-specific SMM 120 may be configured by a respective vendor to create SMOs 130 that may contain information such as ancillary information, and a data stream format such as a group 4 facsimile format, that is proprietary to the respective vendor. That proprietary SMO 130 may be incompatible for use with or by other models of equipment from that same vendor. Further, the proprietary SMO 130 may also be incompatible for use with different vendor SMMs 120, and which may be incompatible with TDPs 140, 142, such as PACS or clinical review workstations 140, 142. TDPs 142 may also be referred to as vendor-specific or modality workstations 142.

The transfer syntax rules may in one exemplary variation establish how ancillary information of such proprietary SMOs 130 (for example, vendor-proprietary DICOM attribute tags) received from SMMs 120 are to be normalized or modified for receipt by other components of the system 100, such as TDPs 140, 142, and other dissimilar vendor SMMs 120. In this way, such transfer syntax rules embody respective SMM 120 and TDP 140, 142 data that establishes one aspect of the compatibility capabilities of the system 100.

Using such transfer syntax rules, the system 100 may more rapidly normalize or modify only those specific elements of the SMOs 130 that must be changed to ensure compatibility between nominally incompatible components. With concise transfer syntax rules, much less data must be normalized or compared and updated to enable such compatibility. This new preferred approach enables higher system throughput and faster communication of SMOs 130 across the system 100 and with SMMs 120, TDPs 140, 142, and other resources 150, 170. In the past, the entire data structure of an SMO 130 was read and then re-formatted in its entirety into a processed and normalized SMO 130 that would be compatible with a target recipient component of the system 100. This less desirable former approach required substantially greater computing power and resources.

Within the DICOM Standard, the transfer syntax is a set of encoding rules that may preferably be applicable to the SMOs 130 of the invention in medical imaging applications. The DICOM transfer syntax enables medical diagnostic vendors, also referred to in the field as Application Entities, who make or sell equipment that communicates medical image information to negotiate common image encoding techniques that they both may preferably support, such as byte ordering and compression. The DICOM standard defines different transfer syntaxes for transferring images across the network or for storing them in files. While establishing a connection for the purposes of transporting diagnostic studies between vendors of Application Entities, the transfer syntax to be employed is typically negotiated between such vendors. Although there is a default transfer syntax that all such vendors are required to support for communication and transmission of diagnostic medical imaging studies, vendors have the flexibility to transmit in multiple transfer syntaxes. This flexibility is intended to enable vendor customers, namely the technologists, users, and clinicians, to have more choices of vendors for their equipment needs, and to take advantage of DICOM compliant compression algorithms that can dramatically reduce the amount of disk storage space required to store patient imaging studies.

In one embodiment of the inventive system 100, the transfer syntax parameter can be created to configure which byte ordering/compression transfer syntax is to be utilized for specific sets of image study transfers and/or communications. This type of syntax transfer application of the system 100 enables users and technologists to achieve en masse or bulk compression transformations of the local or remote archived storage or remote and/or distributed computing resources 150, 170 for on an entire facility or institution to substantially reduce the amount of storage capacity. Bulk encryption and anonymization can also be accomplished to enable protected communications of SMOs across the system 100, distributed computing resources 150, 170, and to other institutions and across industry standard communications interfaces such as the HL7 communications interface (FIG. 1). These capabilities also enable the system 100 to communicate protected/encrypted SMO information as well as anonymized SMO data with health care institutions and organizations using the Health Level 7 or HL7 standards for electronic interchange of clinical, financial, and administrative information among health care oriented computer systems. See, for example, the internet website identified by "www.hl7.org".

In other preferred variations of the MOP 200, commands received from the MC 160 or UISC 165, and/or polling of the parameter databases 180, enable the MOP 200 to obtain a predefined or predetermined mapping parameter, which establishes multi-dimensional mapping protocols. Such mapping protocols enable conversion of the SMO 130 data stream from any given SMM 120 media format and compression standard to a target format and compression standard that may be needed for compatible communications with target devices. Such mapping protocols conversion capabilities may only require conversion of a part or portion of the data stream of the SMO 130, which may significantly reduce the amount of data that must be converted as well as the computing resources needed to process SMOs 130 to be compatible with target devices. These capabilities further increase throughput and speed of the system 100.

The system 100 also contemplated variations to any of the preceding embodiments and configurations wherein the described transfer syntax rules and mapping protocols may be employed by operators via the UISC 165 of the MC 160, or may be invoked by any scheduling parameter. Such actions may also be accomplished in either a batch mode at a predetermined time, or dynamically, on-the-fly, and in real-time as the system 100 receives and processes SMOs 130. Although described in various contexts elsewhere herein, the system 100 also preferably contemplates embodiments wherein multiple MCs 160, UISCs 165, MSSs 190, MOPs 200, schedulers 205, 210, and routers 215 are operating simultaneously with and as part of the system 100 in either locally integrated and/or multithreaded arrangements, and/or in cooperation with multithreaded, remote and distributed processing arrangements using distributed resources 150, 170.

One or more or at least one multimode updater 220 may also be preferably in communication with and/or be a component of the dynamic media object management system 100. The MU 220 may also optionally be a component of and/or capability of the MOP 200. In one possibly preferred embodiment of the system 100, the MU 220 modifies SMOs 130 to update ancillary information and data streams. This update operation may be required to enable the system 100 to update out-of-date elements of new or previously created and stored SMOs 130 with new information. This is often required when changes are needed so that SMOs 130 comply with changes in applicable industry and vendor equipment standards, such as DICOM and PACS, and changing organizational, installation, and institutional data management policies. The latter most often occurs as new collaborative activities and relationships arise between such entities, or when such entities merge or divest from one another.

The optionally preferable MU 220 contemplated for use by the various embodiments of the inventive system 100 also may be operative in one or more or at least one mode(s). One alternatively preferred mode includes, for purposes of illustration but not restriction, a pre-scheduled SMO 130 group or batch update mode wherein an entire store or group of SMOs 130 may be updated. Such updates may occur periodically pursuant to a scheduling parameter communicated to the schedulers 205, 210, or one-time according to a possibly preferred scheduled time and/or date effected by either the MC 160, the UISC 165, or another scheduling parameter communicated to the schedulers 205, 210.

The MU 200 is also optionally capable of other modes of operation that include an on-demand and/or upon-command single batch or real-time updates of selected, queried, or filtered SMOs 130, and/or selected groups of identified, queried, or filtered SMOs 130. The MU 220 may be commanded to execute the update manually by the MC 160 and the UISC 165, or automatically by a scheduling parameter that triggers the update at some predetermined and/or periodic time. An update parameter may also be included in one or more of the parameter databases 180 and may be one or more flexible compare and replace rules and/or a flexible matrix or matrices that identify target information to be queried and replaced, as well as replacement information.

The MU 220 may also optionally include a preferable real-time or dynamic, on-the-fly continuous SMO 130 update mode wherein SMOs 130 are updated during processing by the MOP 200 or as SMOs 130 are communicated or during other processing operations. The MU 220 is more preferably also operative to update and modify SMOs 130 created, generated, and/or stored anywhere within and without the system 100, including whether stored on SMMs 120, TDPs 140, 142, and on remote and/or distributed resources 150, 170. The contemplated modes of operation and flexible update parameters enable the MU 220 to only update specific elements of SMOs 130 instead of the entire SMO 130. As a result, the system 100 can achieve higher throughput and higher speed communications.

For purposes of further detailed illustrations of other possibly preferred embodiments of the dynamic media object and image management system 100, an innovative system and method for the manipulation and management of medical image files is described with continued reference to FIGS. 1, 2, 3, and now also to FIGS. 4, 5, 6, and 7.

For an added example, the system 100 may also include a Graphical User Interface (GUI) that may preferably form a part of the MC 160 and/or the UISC 165. This variant of the GUI, enables the user or technologist to review SMOs 130 to visually discover and rectify DICOM non-conformities that may exist across the many SMMs 120 and TDPs and PACS workstations 140, 142 within their enterprise.

For example, the system 100 can receive, store in the databases 180, and process predefined update parameters for processing SMOs 130. Such update parameters may establish a series of processing rules that enable the user to identify non-conforming ancillary information or DICOM attribute tags, which can be updated by the IOP 200 and/or the MU 220. Further, routing and scheduling parameters stored in the databases 180 can automate and dramatically improve radiology imaging technologist workflows in a Nuclear Medicine department by enabling scheduled dynamic routing of normalized study data or SMOs 130 at a series level to multiple TDPs 140, 142 based on normalized DICOM Attribute Data embedded in the SMOs 130. In one case study, the user realized a 500% productivity gain for its technologists during use and operation of the inventive system 100.

Among the many types of workflow challenges addressed by the system 100, the MSS, ISS 190 and the MOP, IOP 200, are configured to utilize the transfer syntax rules and other predetermined rules and parameters to read the image data and associated DICOM Attribute Tags and ancillary information such as annotations of SMOs 130 in native formats. More specifically, SMOs 130 created, generated, transmitted, and communicated and the respective native formats of the various SMMs 120 can be read, processed, stored, and re-communicated by the system 100.

Once read and stored by the system 100, the native and/or processed SMOs 130 may be further utilized with the GUI of the MC 160 and the UISC 165, as well as the MSS, ISS 190 and the MOP, IOP 200, for user and technologist review. This additional review enables definition of additionally optimized predetermined parameters and processing rules, which can further adjust the data stored in any DICOM Attribute Tag for a particular study contained in one or more SMOs 130.

The stored and processed SMOs 130 may be thereafter further modified, adjusted, reformatted, and communicated on to other DICOM compliant medical imaging devices, SMMs 120, TDPs 140, 142, such as a PACS, modality workstations or viewing stations 142 based on specific scheduling and processing parameters and rules that the technologist and user may have specifically configured for such purposes. Using the contemplated transfer syntax rules already described, the system 100 can process SMOs 130 for communication of imaging studies in the native or preferred format of the target destination TDPs 140, 142, with such transfer syntax processing and conversions being accomplished real-time, dynamically, and "on the fly" at enhanced speed.

In additionally preferred, optional embodiments of the invention 100, the GUI user interface of the MC 160 and UISC 165, a technologist or user having skill in the DICOM standard and implementations defines specific criteria as predetermined parameters, by which to identify a DICOM incompatibility situation among current and legacy SMMs 120. Also defined is a separate or integral matrix that establishes correcting or replacement information that overcomes the incompatibility. These definitions of predetermined parameters and corresponding sets of rules may be used to resolve the data and format inconsistencies of native SMOs 130 in four major ways, including:

1) DICOM Attribute Tag Manipulation: From a workflow perspective, users are able to configure rules to have the MOP, IOP 200 manipulate any DICOM Attribute Tag values of SMOs 130 to resolve DICOM incompatibility issues or integration discrepancies between SMMs 120 and TDPs 140, 142. These DICOM inconsistencies or incompatibilities may be ancillary information of such SMOs 130 in the form of either DICOM Standard Attributes or Private Attribute Tags established by a specific, independent vendor of a SMM 120. An example of this correction and replacement may include adding new DICOM Attributes, modifying a DICOM Attribute value, adding a prefix or suffix to an existing DICOM Attribute, swapping the values of two different DICOM Attributes, deleting a DICOM Attribute, and encrypting a DICOM Attribute's value and any given SMO 130. The system 100 seamlessly incorporates new such processing parameters, rules, correction, and compatibility improving capabilities as they become available.

2) Series Level Routing: Medical diagnostic imaging studies often include multiple series within a study, which is represented by one or more or a series of representational SMOs 130. The MOP, IOP 200 may be configured to dynamically route such studies and corresponding SMOs 130 at the series level using preconfigured rules defined by the user and stored in the parameter databases 180. These SMO 130 encoded series can then be scheduled, again via preconfigured scheduling parameters and associated scheduling rules, for communication and transmission to one or more target destination TDPs 140, 142, which can greatly improve workflow inefficiencies and reduce the usage costs of expensive local and distributed computer resources (i.e. storage, network, CPU, etc) 100, 150, and 170. For each target destination TDP 140, 142, the specified series embodied in the SMOs 130 can have preconfigured DICOM Attribute Tag modification processing parameters and corresponding rules applied to enable the preferred DICOM format of the destination TDP or TDPs 140, 142.

3) Transfer Syntax Discrepancy Resolution: As described briefly elsewhere herein, a Transfer Syntax is a set of encoding rules used to negotiate common encoding techniques such as byte ordering and compression algorithm used between medical device SMMs 120 and TDPs 140, 142 that may need to share information. Using the MC 160 and/or the UISC 165, the user is able configure the system 100 to accept medical diagnostic image data SMOs 130 using a specific vendor SMM 120 preferred syntax, and then communicate those same SMO-based 130 studies using the preferred syntax of the target system TDP 140, 142. This achieves maximum system integration effectiveness. The MOP, IOP 200 contemplated by the invention may support an unlimited number of such transfer syntaxes. For example, one embodiment of the invention that is available from Mach 7 Technologies, Inc. as the Keystone Suite, includes at least ten different transfer syntaxes and compression standards. Those standard transfer syntaxes may include, for purposes of example but not limitation, what those skilled in the relevant field of refer to as: Implicit Value Representation (VR) Little Endian; Explicit Value Representation (VR) Big Endian; Explicit Value Representation (VR) Little Endian; Baseline JPEG; Extended JPEG; Lossless JPEG; Lossless JPEC (psv=1); Lossless JPEG 2000; Lossy JPEG 2000; and Run Length Encoding.

4) Compare/Replace Batch Processing: The system 100 also includes a possible variation of any of the preferred embodiments wherein the MU 220 is configured as a "batch compare" and a "batch replace" component, which operates on a series of predetermined or predefined SMO 130 DICOM Attribute Tags. This variation of the MU 220 enables the user to manipulate and correct DICOM Attribute values in bulk volume. Without this alternatively preferred MU 200 batch of bulk update capability, the technologist or user may be required to make thousands of manual corrections and updates to stored SMOs 130, or to create hundreds of preconfigured rules in processing parameters for storage in the parameter databases 180.

In another optionally preferred variation of any of the inventive system configurations 100, the technologist or user may define update parameters for use by the MU 220 or other components of the system 100, in a text file table, or even in a Microsoft or Sun Microsystems Open Office brand software spreadsheet table. See, e.g., the Mach 7 Technologies Keystone Suite implementation of the inventive system 100. Such a text file and/or spreadsheet may then be imported as a predetermined or predefined processing and/or transfer syntax parameter and/or rule set into the parameter databases 180. Thereafter, in more preferable configurations of the system 100, the technologist or user may then also create a single processing parameter rule in the system 100 to execute the new transfer syntax.

In further alternative variations of the inventive system 100, the GUI of the MC 160 and/or UISC 165, may also preferably include a "first of a kind" graphical workflow diagram that enables technologists to visualize the logical flow associated with the parameterized rules associated with a particular workflow or process or operation of the system 100. This graphical workflow diagram better enables technologists to ensure that predetermined workflow parameters and corresponding rules will result in a successful implementation and more automated workflow.

In the continued example of the system 100 as implemented in a medical imaging workflow application, the MC 160 and/or the UISC 165 includes the GUI to operate the system 100. The MSS, ISS 190 is further configured as a specialized DICOM image server component 190 that, via one of the contemplated network interfaces 110, communicates SMOs 130 such as diagnostic medical image studies created by local or remote SMMs 120 located in radiology, cardiology, and pathology departments.

Such studies embodied in the SMOs 130 are then communicated to IOP 200, which in turn, applies processing and other parameters stored in the databases 180, to the SMOs 130 to detect inconsistencies and incompatibilities in the studies created by the SMMs 120. For each of such studies, the IOP 200 may apply multiple processing, scheduling, and routing parameters and associated transfer syntaxes and other rules to process and modify any or all SMOs 130. Thereafter, the IOP 200 may further communicate the processed studies embodied in the SMOs 130 to other SMMs 120 and/or TDPs 140, 142.

With continued reference to the various figures, and now specifically to FIG. 2, the optionally preferred medical imaging embodiment of the system 100, is depicted to use the aforementioned capabilities to route patient image data and SMOS 130 remotely acquired from SMMs 130 to specified other SMMs 120 and/or TDPs 140, 142 of various clinical care providers. These automated routings are enabled by the technologist or user configured, predetermined scheduling parameters that control the workflow scheduler 210.

With these capabilities, the system 100 may collect a study embodied in an SMO 130 from any medical imaging workstation or TDP 140, 142, or modality or SMM 120. Next, the system 100 may automatically poll the parameter database 180 or other components of the system 100 to obtain one or more scheduling and routing parameters and associated rules from a routing database variation of the parameters databases 180. Additionally, the system 100 may then automatically route the particular study(ies) SMOs 130 to the appropriate station(s) or TDPs 140, 142 based on the schedule and routing rules predetermined by the technologist and/or user.

In other equally desirable configurations of the system 100, the automated scheduling and routing capabilities may also be embodied as manual scheduling and routing capabilities enables by technologist and user command via the MC 160 and /or the UISC 165. Such manual and automated configurations may be established merely by implementation of one or more parameterized scheduling and routing rules that may be entered as needed, and/or stored for automated and manual use in the databases 180. In any of such automated and manual scheduling and routing arrangements, remote clinical review can be easily implemented to employ the services of and computing resources of teleclinicians and tele-radiologists.

Referring now also to FIG. 3, another possibly preferred variation of the system 100 is shown. The dynamic image management system 100 includes the SMMs 120 and the MC 160 among other components described elsewhere herein. The processing workflow of the system 100 may begin with an image or imaging study acquisition modality or SMM 120, which communicates the study or studies as SMOs 130 to the ISS or DICOM services module 190. Only imaging study SMOs 130 from modalities or SMMs 120 that have been registered to the DICOM Services module, for example, via the MC 160 and/or the UISC 165 may be processed.

The DICOM services module 190 receives the image data SMOs 130 and may store the DICOM attribute tags of the SMO 130 within a DICOM attribute relational database variant of the databases 180 for prospective further processing. The IOP 200 and/or the DICOM services module may concurrently and/or thereafter store the full study SMOs 130 within a distributed or remote vendor neutral archive 170. Once a complete study worth of SMOs 130 is communicated, the system 100 and perhaps the IOP 200, a router 215, and/or a scheduler 205, 210, determines whether any routing and/or DICOM attribute tag processing parameters and rules are defined in the parameter databases 180, for the particular SMM 120. If so, the IOP 200 or other system 100 component may poll or query the ISS 190 for new study SMOs 130 that may require further processing.

When new study SMOs 130 are thereby identified, the IOP 200 polls or queries one or more of the databases 180 for all predetermined parameters for the relevant SMM 120 and respective SMOs 130, which parameters define processing (transfer syntax, mapping protocols), scheduling, and routing parameters. Once such predetermined parameters and rules are identified, the IOP 200 automatically processes the SMOs 130 for compatibility with target TDPs 140, 142, such as other SMMs 120, PACS workstations 140, 142, and the like. Thereafter and/or concurrently, the IOP 200 in cooperation with the schedulers 205, 210, and routers 215 communicate the study SMOs 130 to the designated (by the routing parameter(s)) TDPs 140, 142, and other post-processing and archive remote resources 150, 170.

With continued reference to FIG. 3, the dynamic image management system 100 may also incorporate a data services component 230, which can be an independent component, and/or an integral part of the MC 160, UISC 165, and/or IOP 200. Also optionally included may be a messaging queue 240 that communicates with the IOP 200, the ISS 190, and possibly other components of the system 100 to control queuing and processing of newly created study SMOs 130 from the various SMMs 120. More preferably, the IOP 200 polls the messaging queue 240 to ascertain whether newly created study SMOs 130 exist. If so, the IOP 200 and other components process the SMOs 130 as described previously and elsewhere herein.

In additional variations of any of the embodiments of the system 100, the data services component 230 may also be what those skilled in the information technology often term a "web-enabled" interface. This type of interface in simple terms is defined to be any type of interface that can be implemented using world wide web internet browser components commonly known as Microsoft Internet Explorer, Mozilla Firefox, and many others. Such web-enabled interfaces are typically deemed to be easier to implement, have broader compatibility, and greater ease of use for technologists and users of the inventive system 100.

In further alternatively preferred arrangements, the system 100 incorporates the web-enabled data services component 230 configured as a primary data conduit or layer within the arrangement described herein and illustrated in the various figures, including FIG. 3. As may be understood by those having knowledge in the relevant arts, the system 100 thereby further enables, among other capabilities described elsewhere herein, distributed data management, remote task execution, and file and SMO 130 transfer capabilities the various parameter and other databases 180, and other systems, components, equipment, and devices already described. More preferably, the more easily configured, implemented, deployed, maintained, and used web-enabled capabilities of the data services component 230, optimizes the system 100 to utilize the distributed computing resources 150, 170 also described here and known to those skilled in the art.

Figure 4:
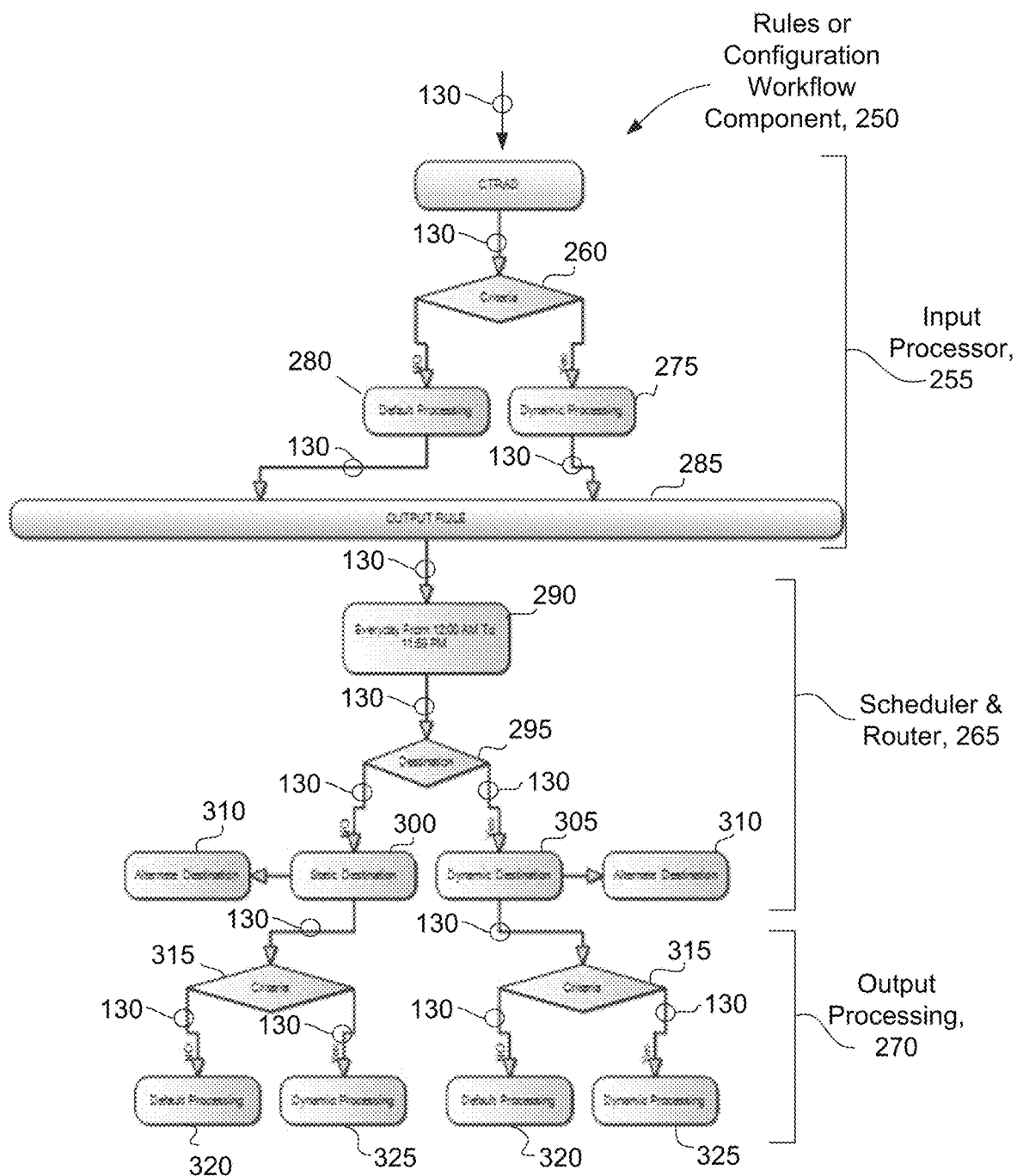
FIG. 4 is an illustration of a component of the dynamic media object management system of FIGS. 1, 2, and 3.

With continued reference to the various figures and now also to FIG. 4, the system 100 may be optionally modified so the MC 160 and/or the UISC 165 or other part of the system 100 further incorporates a configuration workflow component 250 (CWC). The CWC 250 may incorporate and/or embody the graphical workflow element capabilities already described and may enable additional capabilities. Such capabilities further enable the technologist and user to graphically depict the organization and interaction of the various predetermined parameters and the multidimensional corresponding rules and processing procedures, which can also enable better organization and implementation of such parameters and rules and procedures.

The CWC 250 may also preferably be a part of and/or communicate with the data service component 230 and may be visually perceptible to the technologist or user via the GUI interface of the MC 160 and/or UISC 165. Processing and other types of parameters 260 may also be preferably applied to SMOs by an input processor 255 accessed from the MC 160 and/or UISC 165 in the form of an AE (Application Entity) Title Rule Set 252, and as described elsewhere herein. The AE Title Rule Set is known to those with knowledge in the art as a generic title for a DICOM standard compliant construct for a defined set of rules, which corresponds to the processing parameters 260 and associated rules and procedures of the system 100. Technologists and users will typically apply a more meaningful title to such processing parameters 260 other than the generic title "AE Title Rule Set". More preferably, such processing parameters 260 and the corresponding rules represented thereby are typically defined by the technologist and user via the GUI of the MC 160 and/or U ISC 165, or other component of the system 100.

Under the DICOM standard compliant rule set approach, as with the invention of system 100, such processing parameters and rule sets may be categorized into three parts or types of rules or rule sets, based on the specific capabilities and functionality of the respective parameters 260 or rules or procedures. For further example, and with continued reference to FIG. 4, the three categories include: 1) input processing parameters 260 and rules that may preferably be manifested or applied by an input processor 255, 2) scheduling and routing destination parameters 260 that may preferably be manifested or applied by a scheduler and router 265 (similar in operation to the schedulers 205, 210, and router 215), and 3) output processing rules 260 that may preferably be manifested or applied by out processor 270.

For purposes of further illustration without limitation, those skilled in the art may comprehend that such input processing parameters 260 or rules and criteria are conditions that the input processor 255 applies to control what type of processing is applied to a given set of study SMOs 130. For example, certain SMOs 130 will be processed according to either a dynamic or default processing parameter 275, 280 and an output parameter 285. Schedule parameters 290 and routing (destination) parameters 295 or criteria and rules establish how the scheduler and router 265 process the SMOs 130 to static, dynamic, and alternate destinations 300, 305, 310 such as TDPs 140, 142.

The output processor 270 may operate much like the IOP 190 to further apply syntax transfer and protocol mapping parameters to enable compatibility of the SMOs 130 for operation with the target destination TDPs 140, 142.

Figure 5:
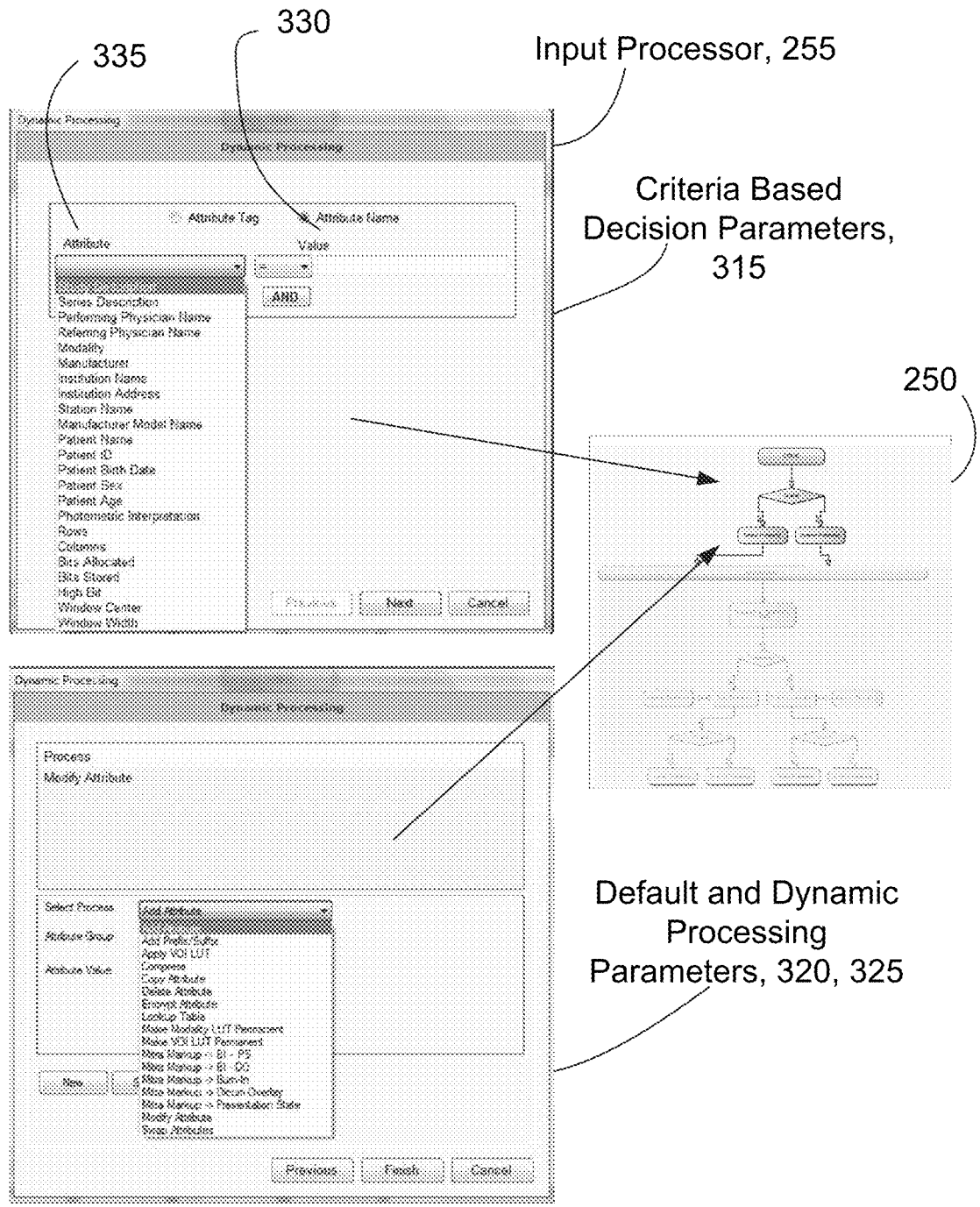
FIG. 5 is an illustration of another component of the dynamic media object management system of the preceding figures.

Referring now also to FIG. 5, another possibly preferred embodiment of the system 100 is depicted wherein the input processor 255 may preferably apply input processing parameters created by the technologist or user via the GUI of the MC 160 and/or the UISC 165. Such input processing parameters and rules may also incorporate predetermine parameters such as criteria-based decision parameters 315 as well as default and dynamic processing parameters 320, 325 and rules that may preferably be applied depending upon the content and detected compatibility and/or deficiencies of a particular study SMO or imaging series or group of representative SMOs 130.

Such criteria-based decision parameters 315 may be directed to evaluate ancillary information or DICOM attribute tag values 325 of the SMOs 130. In additionally preferred embodiments of the parameters 315, the user or technologist may also preferably establish the criteria-based decision parameter 315 to evaluate the ancillary information or the DICOM standard attribute tag value 325 and/or any other value of such an attribute as established by other DICOM standard attribute tag values that may include group, element numbers and other DICOM information 330 from a DICOM standard or specific system 100 data dictionary.

These additional and optional but possibly preferred capabilities enable the technologist and user to create predetermined parameters that can evaluate a large possible variety of vendor-proprietary DICOM attribute tags in setting up criteria parameters. In turn, this added capability further enables the inventive system 100 to establish heretofore unavailable compatibility between various legacy and current day SMMs 120 and TDPs 140, 142.

Those skilled in the relevant fields of technology may comprehend that multiple criteria-based parameters 315 and similarly capable such predetermined parameters may preferably be applied in sequence and/or cascaded together to establish more complex, sophisticated, and effective dynamic processing and management capabilities of SMOs 130. For further example, one such cascaded approach can be applied wherein default parameters 320 and/or dynamic processing parameters 325 (FIG. 4) can be applied to the SMOs 130 depending SMO content (depending upon detected inconsistencies or incompatibilities) upon after the preceding processing by the decision parameters 315.

Another exemplary operational application of the inventive system 100 may further illustrate the capabilities of the system 100 in real-world scenarios. In a rural area of the United States, two hospitals, Metro East and Metro West, currently operate independently with each facility having implemented medical imaging SMMs and TDPs from competing and nominally incompatible vendors. Each such vendor has employed proprietary variations of purported DICOM standard compliant infrastructure. The two hospitals agree to open a jointly owned Ambulatory Care Center (ACC), where medical imaging studies are performed (SMOs are created by the respective SMMs). The study SMOs are to be stored, analyzed, and diagnosed by technologists and/or clinicians on the TDPs or PACS workstations at Metro East.

However, it is discovered that when prior study SMOs from Metro West are needed at Metro East for historical comparisons by the clinicians or technologists, DICOM incompatibilities between the respective PACS systems of East and West prevent use of historical information due to incompatibilities between the respective vendor DICOM ancillary information or DICOM attribute tags. Specifically, edited annotations from Metro West are not displaying properly on the Metro East TDPs or PACS workstations. This incompatibility impedes diagnoses protocol, which require comparisons between historical image studies when analyzing or reading and diagnosing new imaging studies.

In using the inventive system 100 to troubleshoot this medical imaging compatibility and workflow issue, it is determined that studies or SMOs created on the Metro West SMMs have incorporated annotations using what is known to those skilled in the art as the "ABC Meca Markup 2.0 QC" system (a fictitious name). Those skilled in the art may comprehend that such annotations are graphics that are overlaid by the technologist or clinician to amplify a diagnosis with graphical highlighting or markups, which are embedded in the ancillary information or DICOM attribute tags of the SMOs 130, which are also sometimes referred to as DICOM attribute overlay or presentation tags. Further investigation revealed that the Metro West ancillary information was converted by the vendor to a non-DICOM conforming format. As a result, the Metro East TDPs or PACS workstation improperly displayed the annotations, which impeded the diagnoses of the new imaging studies.

Using the aforementioned features and capabilities of the inventive system 100, the non-DICOM standard conforming elements of the Metro West ancillary information or attribute tags was graphically displayed by the GUI of the MC 160 and/or the UISC 165 and a new predetermined parameter was created that included a criteria-based decision parameter, which evaluated each SMO 130 for the non-compliant ancillary information. Another predetermined parameter was created that established a transfer syntax parameter, which enabled the IOP 190 to compare and replace the non-conforming elements of the SMOs 130 with DICOM compliant ancillary information.

As a result, when Metro East TDPs or PACS workstation queried study SMOs created by the ACC that are stored at Metro West, the system 100 dynamically updates the non-DICOM compliant SMOs 130 on-the-fly or in real-time so that the SMOs 130 are compatibly displayed on the Metro East TDPs or PACS workstations. Very high-throughput and communications speeds are enabled since the transfer syntax parameter was designed by the technologist or clinician to only replace those specific, non-compliant, annotation elements of the ancillary information or DICOM attribute tags with compliant information. In effect, the system 100 thereby requires minimal computing resources, and efficiently manages the SMO incompatibility transparently, automatically, and in real-time so that the technologists and clinicians can now focus on their diagnoses.

Figure 6:
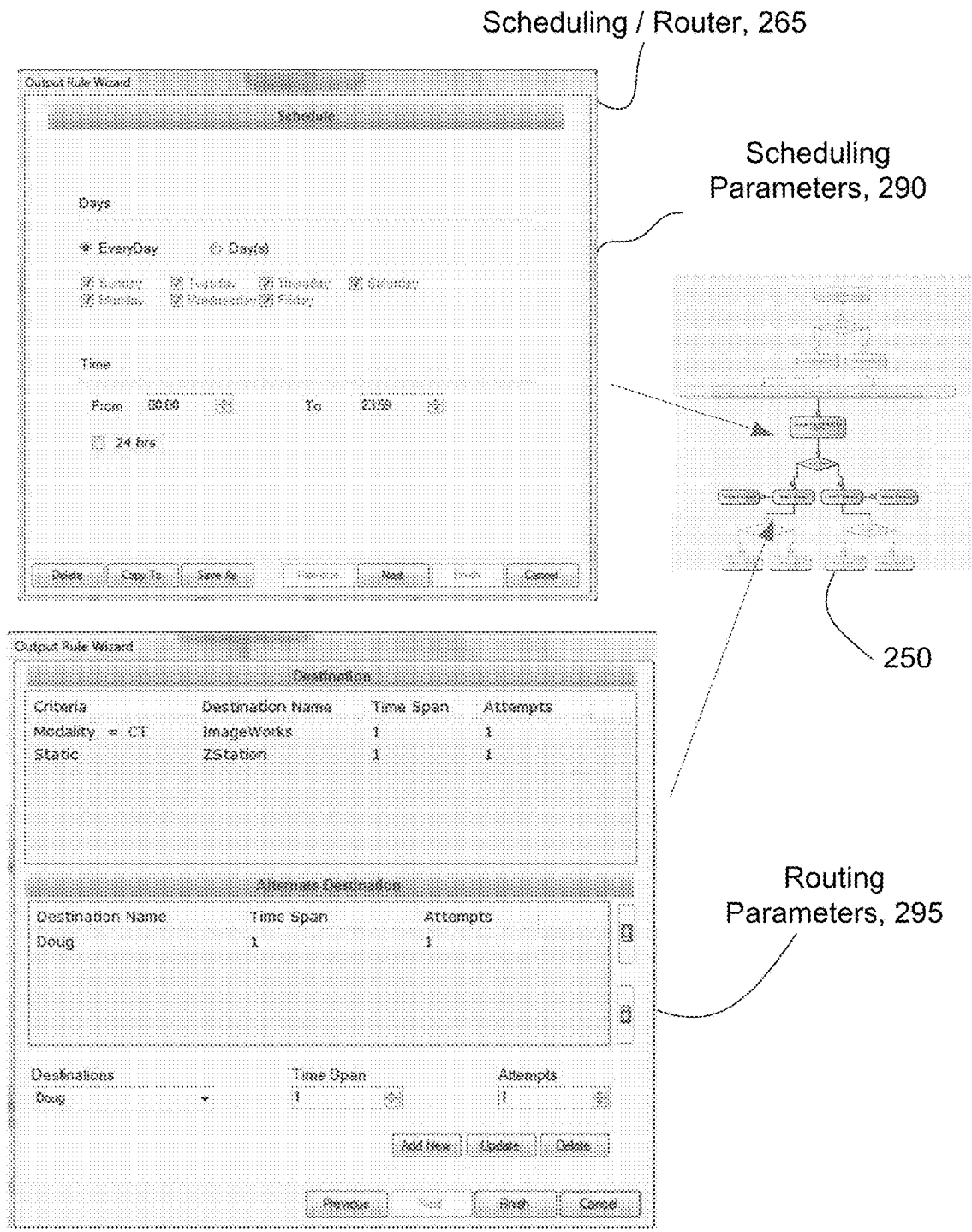
FIG. 6 is an illustration of yet another element of the dynamic media object management system of the preceding figures.

With continued reference to the various figures and now also to FIG. 6, the operation of the scheduler/router or schedule and routing processor 265 is depicted in an optionally preferred arrangement and in an exemplary embodiment for purposes of further explanation, but not limitation. The scheduler/router 265 may be configured by schedule or scheduling parameters 290 that may be created via the GUI of the MC 160 and/or UISC 165 exemplified in FIG. 6, and can be selected from a series of such scheduling parameters 290. Additionally, various elements of such schedule parameters may be adjusted as needed and any combination of preferred times and dates may be established for the respective schedule parameter 290.

Similarly, the scheduler/router may be configured for preferred routing of SMOs 130 by routing parameters 295 that may be created via the GUI of the MC 160 and/or UISC 165 exemplified in FIG. 6, and can be selected from a series of such routing parameters that may preferably represent those target TDPs 140, 142, and SMMs 120 registered in the system 100 for communicating such SMOs 130.

Those who are skilled in the medical imaging and diagnostic arts may be able to comprehend that creation or acquisition of patient imaging studies from a modality such as SMMs 120, is only a first step in the total workflow required for achieving an effective, medical-image-based diagnosis of medical conditions. In addition to creating or acquiring the imaging study, prompt analysis of the study is required by competent, qualified professional clinicians and technologists, such as radiologists skilled and licensed to provide diagnostic opinions on the images obtained from the specific type of modality or SMM device.

As specialty radiologists are often difficult to maintain at full capacity at all diagnostic imaging centers, the practice of 'remote reading', or tele-radiology has become an accepted and widespread approach for providing the correct radiology talent for specific types of medical imaging studies. However, communicating such diagnostic medical imaging studies to the right tele-radiologist location is a challenge. Such studies are electronically embodied in very large file sizes and may consist of a large number of such files (SMOs 130) where a large series of images may be needed to evaluate a large anatomical region.

Accordingly, the various optionally preferred embodiments of the inventive system 100 contemplate very flexible routing parameter 295 capabilities wherein the best possible radiologist can be dynamically identified based on the DICOM compliant ancillary information or attribute tags of the SMOs 130, as well as any other conceivable criteria. For example, consider exigent circumstances that may require a rapid analysis of an imaging study at an unusual hour in one part of the world where most radiologists may not be immediately available due to the local time. The system 100 can poll schedule parameters 290 in the parameter databases 180 to understand such time of day constraints. In turn, the system 100 may then poll the routing parameters 295 to identify a geographically disparate radiologist across the world that may be electronically available to receive the imaging study SMOs at that time. Utilizing these parameters 290, 295, the system 100 can dynamically, transparently, and automatically route the imaging study SMOs 130 to a more readily available radiologist who may be identified by the routing parameter 295 as being capable of offering a rapid turn-around analysis. The system 100 also enables the technologist or clinician to query and manually identify such parameters and opportunities, so as to enable a further measure of peace of mind to those confronted with such exigencies. In a further preferable example, such schedule and routing parameters 290, 295 may also be configured to automatically and manually enable the scheduling and routing of simultaneous and/or concurrent such routings to enable more rapid communications where multiple opinions may be needed. In this optionally preferred configuration, such image study SMOs 130 may be automatically communicated to one or more reviewing radiologists for multiple opinions.

With reference now also to FIG. 7, another alternative variation to any of the preceding embodiments of the system 100 is depicted wherein the operation of a preferably optional output processor 270 is shown with more exemplary details. As with earlier illustrative examples, the output processor 270 applies the criteria-based decision parameters 315 to identify SMOs 130 for further processing. Further processing may, for purposes of example, include application of one of the transfer syntax and/or mapping protocol parameters so as to ensure compatibility of the image study SMOs 130 with the target destination TDPS 140, 142, SMMs, 120, or other systems like the inventive system 100.

INDUSTRIAL APPLICABILITY

The embodiments of the present invention are suitable for use in many applications that involve highly optimized throughput and management, or optimally high speed communication and or modification of electronically embodied media objects, such as images, sequences of images, audio data such as recorded audio information, audiovisual information such as video data, textually based information, and all conceivable combinations thereof.

The many optional and preferred configurations of the inventive media object management system can be modified to accommodate nearly any conceivable type of such legacy, current, and prospective media objects, regardless of the optionally preferable types of specialized and general purpose information technology infrastructure that is preferred for use in operation.

In medical imaging applications, the imaging media object management system that embodies the invention enables vendor neutral compatibility across many types of previously incompatible legacy and more current imaging modalities and medical professional and technologist reviewing workstations and infrastructure.

Additionally, for voice transcription media object management embodiments of the invention, the novel audio media object management system optimizes the compatibility of many types of voice-to-analog and voice-to-digital audio transcription equipment with an unlimited number of computer-automated and human-in-the-loop audio transcription devices, so as to enable high speed processing and transcription of data files containing such audio information.

Video processing service, equipment, system, news, and entertainment providers also benefit from the new media object management system because they can now better leverage legacy systems while availing themselves of the advantageous optimized throughput capabilities of the invention.

Similarly, purveyors of text-based media as well as those organizations and individuals that use combinations of text, audio, image, and audiovisual media, can now better enable communications between legacy and newer systems without impediment.

The preferred, optional, and modified and alternative arrangements of the invention are also capable of easily establishing compatibility with the many currently contemplated, prospective innovations in the relevant fields of technology of the invention.

Accordingly, even though only few such embodiments, alternatives, variations, and modifications of the present invention are described and illustrated herein, it is to be understood that the practice of such additional modifications and variations and the equivalents thereof, are within the spirit and scope of the invention as defined in the following claims.

The invention claimed is:

1. A dynamic media object management system in communication with at least one source media modality (SMM) and at least one technologist data processor (TDP) and adapted to communicate source media objects (SMOs) there between, comprising:
at least one parameter database and at least one management console (MC), wherein said at least one MC includes a user interactive subsystems controller (UISC) in communication with said at least one parameter database, wherein said at least one parameter database is configured for storing predetermined parameters received from said UISC;
at least one modality services subsystem (MSS) in communication with said at least one management console wherein said MSS is operative to communicate the SMOs, wherein said SMOs as communicated from said MSS are in a format incompatible with said at least one TDP, wherein said SMOs as communicated by said MSS include compliant SMO elements and non-compliant SMO elements, wherein the compliant SMO elements are compliant with the TDP, and wherein the non-compliant SMO elements are non-compliant with the TDP;
at least one media object processor (MOP) interoperable with said at least one MC and said MSS, wherein said at least one MOP is connected to dynamically receive SMOs from said MSS and normalize the SMOs on the fly; and
wherein said at least one MOP is connected to apply a plurality of said predetermined parameters to said SMOs to normalize said SMOs, wherein said at least one MOP is connected to route the normalized SMOs to the at least one TDP according to a predetermined routing parameter and according to at least one predetermined mapping parameter, wherein said predetermined routing parameter and said at least one predetermined mapping parameter are communicated to said MOP from said at least one parameter database, wherein said at least one MOP is responsive to said at least one predetermined mapping parameter, wherein said at least one predetermined mapping parameter establishes a mapping protocol operative with said MOP and enabling compatible communication of the mapped and normalized SMOs to the at least one TDP, wherein said applying a plurality of said predetermined parameters by said processor changes format of the non-compliant SMO elements into now-compliant SMO elements, wherein said applying a plurality of said predetermined parameters by said processor avoids spending processing time on a plurality of the compliant SMO elements to speed processing, wherein said applying a plurality of said predetermined parameters by said processor provides said format changing at a speed in real time with the communication of the SMO from the MSS to the TDP.

2. The dynamic media object management system according to claim 1, further comprising a predetermined schedule parameter, wherein the at least one MOP further includes at least one scheduler responsive to said predetermined schedule parameter for scheduling receipt and processing said media object.

3. The dynamic media object management system according to claim 1, wherein said at least one MOP further includes at least one router responsive to said predetermined routing parameter to route the normalized SMOs to one or more of the at least one TDP.

4. The dynamic media object management system according to claim 1, further comprising at least one predetermined transfer syntax parameter, wherein said at least one MOP is responsive to said at least one predetermined transfer syntax parameter, wherein said at least one predetermined transfer syntax parameter establishes a transfer syntax operative with said MOP to normalize the SMOs to enable compatible communication of the normalized SMOs to the at least one TDP.

5. The dynamic media object management system according to claim 1, further comprising at least one predetermined transfer syntax parameter, wherein said at least one MOP is responsive to said at least one predetermined transfer syntax parameter, wherein said at least one predetermined transfer syntax parameter establishes a transfer syntax operative with said MOP to normalize the SMOs.

6. The dynamic media object management system according to claim 1, wherein each of the SMOs includes a target element, and wherein said at least one MOP further includes a multimode updater (MU) responsive to at least one update parameter, wherein the at least one update parameter enables said MU to update the target elements of the SMOs.

7. The dynamic media object management system according to claim 6, wherein the MU is configured to dynamically update the target elements of the SMOs as the SMOs are processed by said MOP before communicating the normalized and mapped SMOs to the at least one TDP.

8. The dynamic media object management system according to claim 6, wherein said MU is configured to batch update the target elements of the SMOs in response to a user command received from the UISC.

9. A dynamic media object management system, in communication with at least one source media modality (SMM) and at least one technologist data processor (TDP) and adapted to communicate source media objects (SMOs) there between, wherein the SMOs each have at least one target element, comprising:
at least one parameter database and at least one management console (MC), wherein said at least one MC includes a user interactive subsystems controller (UISC) in communication with said at least one parameter database, wherein said at least one parameter database stores predetermined parameters received from the UISC;
at least one modality services subsystem (MSS) in communication with said at least one management console wherein said MSS is operative to communicate the SMOs, wherein said SMOs as communicated from said MSS are in a format incompatible with said at least one TDP, wherein said SMOs as communicated by said MSS include compliant SMO elements and non-compliant SMO elements, wherein the compliant SMO elements are compliant with the TDP, and wherein the non-compliant SMO elements are non-compliant with the TDP;
at least one media object processor (MOP) interoperable with said at least one MC and said MSS, wherein said at least one MOP includes a multimode updater (MU) responsive to at least one update parameter that enables said MU to update the at least one target element of each of the SMOs; and
wherein said at least one MOP is connected to dynamically receive SMOs from said MSS and normalize the SMOs on the fly using at least one of the predetermined parameters and routes the normalized SMOs to the at least one TDP according to a predetermined routing parameter and according to at least one predetermined mapping parameter, wherein said predetermined routing parameter and said at least one predetermined mapping parameter are communicated from said at least one parameter database, wherein said at least one MOP is responsive to at least one predetermined transfer syntax parameter that establishes a transfer syntax operative with said MOP to normalize the SMOs on the fly, and wherein said at least one MOP is also responsive to at least one predetermined mapping parameter, wherein said at least one predetermined mapping parameter establishes a mapping protocol operative with said MOP, and enabling said MOP to compatibly communicate normalized and mapped SMOs to the at least one TDP, wherein said applying a plurality of said predetermined parameters by said processor changes format of the non-compliant SMO elements into now-compliant SMO elements, wherein said applying a plurality of said predetermined parameters by said processor avoids spending processing time on a plurality of the compliant SMO elements to speed processing, wherein said applying a plurality of said predetermined parameters by said processor provides said format changing at a speed in real time with the communication of the SMO from the MSS to the TDP.

10. A dynamic image management system in communication with at least one imaging modality and at least one image review workstation (IRW) and adapted to communicate image media objects (IMOs) there between, comprising:
at least one parameter database and at least one management console (MC), wherein said at least one MC includes a user interactive subsystems controller (UISC) in communication with said at least one parameter database, wherein said at least one parameter database stores predetermined parameters received from the UISC;
at least one image services subsystem (ISS) in communication with said at least one management console wherein said ISS is operative to communicate the IMOs, wherein said IMOs as communicated from said ISS are in a format incompatible with said at least one IRW, wherein said IMOs as communicated by said ISS include compliant IMO elements and non-compliant IMO elements, wherein the compliant SMO elements are compliant with the IRW, and wherein the non-compliant SMO elements are non-compliant with the IRW;
at least one image object processor (IOP) interoperable with said at least one MC and said ISS; wherein said at least one IOP is connected to dynamically receive IMOs from said ISS and normalize the IMOs on the fly; and
wherein said at least on IOP is connected to apply a plurality of said predetermined parameters to said IMOs to normalize said IMOs, wherein said at least one IOP is connected to route the normalized IMOs to the at least one IRW according to a predetermined routing parameter and according to at least one predetermined mapping parameter, wherein said predetermined routing parameter and said at least one predetermined mapping parameter are communicated to said IOP from said at least one parameter database, wherein said at least one IOP is responsive to said at least one predetermined mapping parameter, wherein said at least one predetermined mapping parameter establishes a mapping protocol operative with said IOP and enabling compatible communication of the mapped and normalized IMOs to the at least one IRW, wherein said applying a plurality of said predetermined parameters by said processor changes format of the non-compliant IMO elements into now-compliant IMO elements, wherein said applying a plurality of said predetermined parameters by said processor avoids spending processing time on a plurality of the compliant IMO elements to speed processing, wherein said applying a plurality of said predetermined parameters by said processor provides said format changing at a speed in real time with the communication of the IMO from the ISS to the IRW.

11. The dynamic media object management system according to claim 10, further comprising a predetermined schedule parameter, wherein said at least one IOP further includes at least one scheduler responsive to said predetermined schedule parameter, wherein said at least one scheduler establishes a predetermined time to communicate the normalized IMOs to the at least one IRW.

12. The dynamic media object management system according to claim 10, further comprising said predetermined routing parameter, wherein said at least one IOP further includes at least one router responsive to said predetermined routing parameter to route the normalized IMOs to one or more of the at least one IRW.

13. The dynamic media object management system according to claim 10, further comprising at least one predetermined transfer syntax parameter, wherein said at least one IOP is responsive to said at least one predetermined transfer syntax parameter, wherein said at least one predetermined transfer syntax parameter establishes a transfer syntax operative with said IOP to normalize the IMOs to enable compatible communication of the normalized IMOs to the at least one IRW.

14. The dynamic media object management system according to claim 10, further comprising said at least one predetermined mapping parameter, wherein said at least one IOP is responsive to said at least one predetermined mapping parameter, wherein said at least one predetermined mapping parameter establishes a mapping protocol operative with said IOP and enabling compatible communication of the normalized and mapped IMOs to the at least one IRW.

15. The dynamic media object management system according to claim 10, further comprising at least one predetermined transfer syntax parameter and at least one predetermined mapping parameter, wherein said at least one IOP is responsive to said at least one predetermined transfer syntax parameter, wherein said at least one predetermined transfer syntax parameter establishes a transfer syntax operative with said IOP to normalize the IMOs, and wherein said at least one IOP is also responsive to said at least one predetermined mapping parameter, wherein said at least one predetermined mapping parameter establishes a mapping protocol operative with said IOP and wherein said IOP communicates compatible normalized and mapped IMOs to the at least one IRW.

16. The dynamic media object management system according to claim 10, wherein each of the IMOs includes at least one target element, and wherein said at least one IOP further includes a multimode updater (MU) responsive to at least one update parameter, wherein said at least one update parameter enables said MU to update the at least one target element of each of the IMOs.

17. The dynamic media object management system according to claim 16, wherein said MU is configured to dynamically update the at least one target element of each of the IMOs as the IMOs are processed by the IOP before communicating said normalized and mapped IMOs to the at least one IRW.

18. The dynamic media object management system according to claim 16, wherein said MU is configured to batch update the target elements of the IMOs in response to a user command received from the UISC.

19. The dynamic media object management system according to claim 10, further comprising said at least one predetermined routing parameter, at least one predetermined transfer syntax parameter, and said at least one predetermined mapping parameter, wherein said at least one IOP is responsive to said at least one predetermined routing parameter to route the IMOs to one or more of the at least one IRW, wherein said at least one IOP is responsive to said at least one predetermined transfer syntax parameter, wherein said at least one predetermined transfer syntax parameter establishes a transfer syntax operative with said IOP to normalize the IMOs, and wherein said at least one IOP is also responsive to said at least one predetermined mapping parameter, wherein said at least one predetermined mapping parameter establishes a mapping protocol operative with said IOP, and wherein said IOP communicates compatible normalized and mapped IMOs to the at least one IRW.

20. A method of operating a system for communicating a media object from a sending system to a receiving system, comprising:
   a. providing the sending system and the receiving system, wherein the sending system provides media objects in a first format and wherein the receiving system is compatible with media objects in a second format, wherein the receiving system is incompatible with media objects in the first format;
   b. providing a processor connected to the sending system and to the receiving system;
   c. transmitting the media object from the sending system to said processor, wherein the media object has the first format, wherein the media object as sent by the sending system includes compliant media object elements and non-compliant media object elements, wherein the compliant media object elements are compliant with the second format, and wherein the non-compliant media object elements are non-compliant with the second format;
   d. providing a data base having at least one rule for changing format of media objects;
   e. providing said at least one rule from said data base to said processor;
   f. on-the-fly changing the media object from the first format to the second format based on applying said at least one rule provided to said processor, wherein said applying said at least one rule by said processor changes format of the non-compliant media object elements into now-compliant media object elements, wherein said applying said at least one rule avoids spending processing time on a plurality of the compliant media object elements to speed processing;
   g. providing a data base having a plurality of predetermined routing parameters and at least one of said predetermined routing parameters to said processor; and
   h. transmitting said on-the-fly format-changed media object in said second format to the receiving system, wherein said transmitting said format-changed media object is according to at least one of said predetermined routing parameters, wherein said applying said at least one rule provides said format changing at a speed in real time with the communication of the media object from the sending system to the receiving system.

21. The method as recited in claim 20, wherein said processor uses said at least one rule to normalize format of said media object for providing compatible communication of a normalized media object to a plurality of receiving systems.

22. The method as recited in claim 21, further comprising a plurality of sending systems and said plurality of receiving systems, wherein at least one from the group consisting of said plurality of sending systems include sending systems that have incompatible media object formats and said plurality of receiving systems include receiving systems that have incompatible media object formats.

23. The method as recited in claim 20, further comprising providing a display for displaying a user interface, and providing input to said user interface for defining one of said plurality of rules.

24. The method as recited in claim 23, wherein said user interface includes a graphical user interface.

25. The method as recited in claim 20, wherein said data base having at least one rule for translating format of media objects includes a parameter database, further comprising providing a user interactive subsystems controller in communication with said parameter database, wherein said at least one rule includes predetermined parameters in said parameter data base, further comprising inputting predetermined parameters at said user interactive subsystems controller and transferring said predetermined parameters from said user interactive subsystems controller to said parameter database.

26. The method as recited in claim 20, further comprising providing a media object queue, further comprising communicating said media objects with said media object queue.

27. The method as recited in claim 25, further comprising dynamically receiving a media object with said processor and changing said media object using at least one of said predetermined parameters.

28. The method as recited in claim 27, further comprising transmitting said translated media object according to a predetermined schedule parameter.

29. The method as recited in claim 28, wherein said processor includes a scheduler, further comprising providing said predetermined schedule parameter to said scheduler and establishing a predetermined time for receipt and processing said media object.

30. The method as recited in claim 20, wherein said processor includes a router, further comprising providing said predetermined routing parameter to said router and routing said media object.

31. The method as recited in claim 28, further comprising providing a predetermined transfer syntax parameter and changing said media object with said predetermined transfer syntax parameter.

32. The method as recited in claim 28, further comprising providing a predetermined mapping parameter, establishing a mapping protocol with said predetermined mapping parameter, and enabling compatible communication of said translated media object to said receiving system with said mapping protocol.

33. The method as recited in claim 20, wherein said media object further includes a target element, further comprising providing an updater parameter to said processor, further comprising updating said target element with said updater parameter.

34. The method as recited in claim 33, wherein said media object processor includes a multimode updater, further comprising dynamically updating said target element with said multimode updater as said media object is processed in said processor and before communicating said media object from said processor.

35. The method as recited in claim 33, further comprising providing a user interactive subsystems controller and updating said target element in response to a user command received from said user interactive subsystems controller.

36. The method as recited in claim 20, wherein said media object includes an image media object.

37. The method as recited in claim 36, wherein said sending system includes an imaging device and wherein said receiving system includes an image review workstation, wherein said changing format allows said imaging device to communicate said image media object for viewing on said image review workstation.

38. The method as recited in claim 37, further comprising dynamically receiving said image media object, providing a schedule parameter from a database to said image object processor, and on the fly changing format of said image media object using said at least one rule for changing format of media objects, and routing said format-changed image media object according to said predetermined routing and schedule parameters.

39. The method as recited in claim 38, wherein said processor includes a scheduler, further comprising providing said predetermined schedule parameter to said scheduler and establishing a predetermined time for receipt and processing said media object.

40. The method as recited in claim 38, wherein said processor includes a router, further comprising applying said predetermined routing parameter to said router and routing said translated media object to said image review workstation.

41. The method as recited in claim 38, further comprising providing a predetermined transfer syntax parameter, wherein said changing format includes establishing a transfer syntax to normalize said image media object to enable compatible communication of said image media object to said image review workstation, and changing format of said image media object by applying said predetermined transfer syntax parameter in said processor.

42. The method as recited in claim 38, further comprising providing a predetermined mapping parameter, establishing a mapping protocol with said predetermined mapping parameter, and communicating said translated and mapped image media object to said image review workstation.

43. The method as recited in claim 38, further comprising providing a predetermined update parameter, wherein said processor further includes a multimode updater, wherein said image media object includes a target element, wherein said update parameter enables said multimode updater to update said target element, further comprising providing said update parameter to said processor and updating said target element.

44. The method as recited in claim 38, wherein said image media object includes a target element, further comprising dynamically updating target elements of a plurality of said image media objects as said image media objects are processed by said processor before communicating said translated image media object to said image review workstation.

45. The method as recited in claim 38, further comprising providing a user interactive subsystems controller and providing a user command from said user interactive subsystems controller to said processor and updating said target elements in response to said user command.

* * * * *